United States Patent
Zhang et al.

(10) Patent No.: US 11,407,711 B2
(45) Date of Patent: Aug. 9, 2022

(54) BENZAMIDE COMPOUND AND USE THEREOF

(71) Applicant: METISA BIOTECHNOLOGY CO., LTD., Guangxi (CN)

(72) Inventors: Lixin Zhang, Liaoning (CN); Jing Zhang, Liaoning (CN); Xihan Zhang, Liaoning (CN); Yixing Gao, Liaoning (CN); Jie Wang, Liaoning (CN); Zhuo Kang, Liaoning (CN)

(73) Assignee: METISA BIOTECHNOLOGY CO., LTD., Guangxi (CN)

( * ) Notice: Subject to any disclaimer, the term of this patent is extended or adjusted under 35 U.S.C. 154(b) by 85 days.

(21) Appl. No.: 17/054,259

(22) PCT Filed: May 7, 2019

(86) PCT No.: PCT/CN2019/085737
§ 371 (c)(1),
(2) Date: Nov. 10, 2020

(87) PCT Pub. No.: WO2019/214588
PCT Pub. Date: Nov. 14, 2019

(65) Prior Publication Data
US 2021/0238126 A1   Aug. 5, 2021

(30) Foreign Application Priority Data
May 11, 2018 (CN) .......................... 201810448081.X

(51) Int. Cl.
| | |
|---|---|
| *C07C 255/29* | (2006.01) |
| *A01N 37/22* | (2006.01) |
| *A01N 37/34* | (2006.01) |
| *C07C 237/40* | (2006.01) |
| *C07C 255/57* | (2006.01) |
| *A01N 37/46* | (2006.01) |

(52) U.S. Cl.
CPC ............ *C07C 255/29* (2013.01); *A01N 37/22* (2013.01); *A01N 37/34* (2013.01); *C07C 237/40* (2013.01)

(58) Field of Classification Search
CPC ... C07C 255/29; C07C 237/40; C07C 255/57; A01N 37/22; A01N 37/34; A01N 37/46
See application file for complete search history.

(56) References Cited

U.S. PATENT DOCUMENTS
2011/0201687 A1   8/2011 Kobayashi et al.

FOREIGN PATENT DOCUMENTS

| | | |
|---|---|---|
| CN | 1926094 A | 3/2007 |
| CN | 102112437 A | 6/2011 |
| CN | 102119143 A | 7/2011 |
| CN | 102119144 A | 7/2011 |
| JP | 2007099761 A | 4/2007 |
| JP | 2010-513346 A | 4/2010 |
| JP | 2011063549 A | 3/2011 |
| JP | 2012-526066 A | 10/2012 |
| WO | 2005021488 A1 | 3/2005 |
| WO | 2005073165 A1 | 8/2005 |
| WO | 2006137395 A1 | 12/2006 |
| WO | 2008000438 A1 | 1/2008 |
| WO | 2008074427 A8 | 6/2008 |
| WO | 2008107091 A8 | 9/2008 |
| WO | 2010013567 A1 | 2/2010 |
| WO | 2010018714 A1 | 2/2010 |
| WO | 2010018857 A1 | 2/2010 |
| WO | 2010090282 A1 | 8/2010 |
| WO | 2010127926 A1 | 11/2010 |
| WO | 2010127928 A1 | 11/2010 |
| WO | 2011093415 A1 | 8/2011 |
| WO | 2012020483 A1 | 2/2012 |
| WO | 2012020484 A1 | 2/2012 |
| WO | 2012077221 A1 | 6/2012 |
| WO | 2012164698 A1 | 12/2012 |
| WO | 2013050261 A1 | 4/2013 |
| WO | 2014067838 A1 | 5/2014 |
| WO | 2014069665 A1 | 5/2014 |
| WO | 2014161848 A1 | 10/2014 |
| WO | 2014161849 A1 | 10/2014 |
| WO | 2014161850 A1 | 10/2014 |
| WO | 2015097091 A1 | 7/2015 |
| WO | 2015097094 A1 | 7/2015 |
| WO | 2017104838 A1 | 6/2017 |

OTHER PUBLICATIONS

International Search Report issued in corresponding International Application No. PCT/CN2019/085737; dated Jul. 25, 2019; 8 pgs.
Search Report issued is related Chinese Application No. 2019103738706; dated Mar. 28, 2020; 3 pgs.

*Primary Examiner* — Trevor Love
(74) *Attorney, Agent, or Firm* — Hauptman Ham, LLP

(57) ABSTRACT

The present disclosure relates to a benzamide compound as shown in Formula I, an insecticidal comprising same, and a use of the compound as an insecticide in the fields of agriculture, forestry and health.

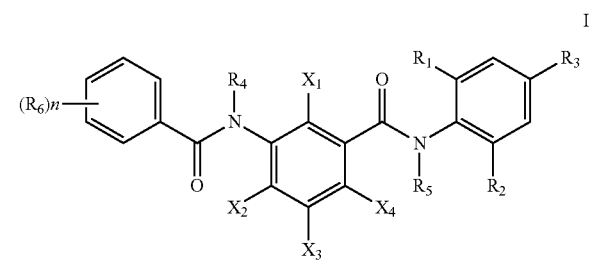

7 Claims, No Drawings

BENZAMIDE COMPOUND AND USE THEREOF

RELATED APPLICATIONS

The present application is a National Phase of International Application Number PCT/CN2019/085737 filed May 7, 2019 and claims priority to Chinese Application Number 201810448081.X filed May 11, 2018.

FIELD OF THE INVENTION

The present invention belongs to the field of agricultural insecticides; and particularly relates to a novel benzamide compound and use thereof.

BACKGROUND OF THE INVENTION

The patent JP2007099761A relates to a benzamide compound having insecticidal activity, and specifically discloses the following structure: CK1 (compound No. 1-23), CK2 (compound No. 1-24), CK3 (compound No. 1-206).

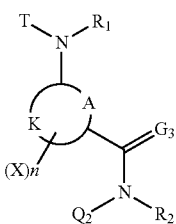

CK1

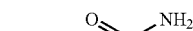
CK2

CK3

The patent CN102112437A discloses a compound represented by the following Formula and specific compounds CK4 (compound No. 6-18), CK5 (compound No. 1-128), CK6 (compound No. 1-163), CK7 (compound No. 1-171), CK8 (compound No. 7-130), CK9 (compound No. 7-135), CK10 (compound No. 7-169), CK11 (compound No. 7-174), CK12 (compound No. 8-111), CK13 (compound No. 8-146), CK14 (compound No. 8-155), having certain insecticidal activity:

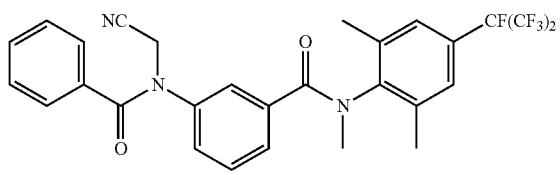

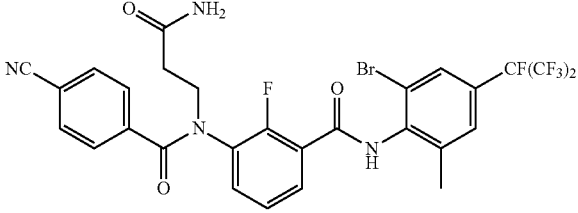
CK4

CK5

CK6

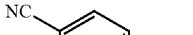
CK7

CK8

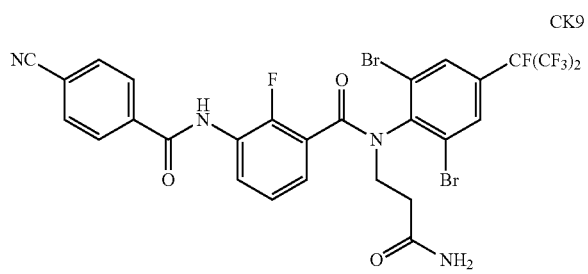
CK9

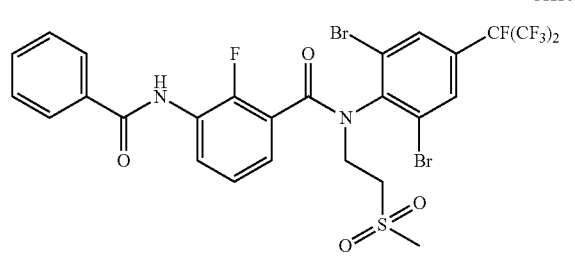
CK10

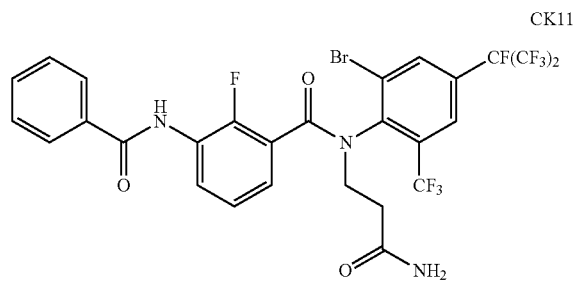
CK11

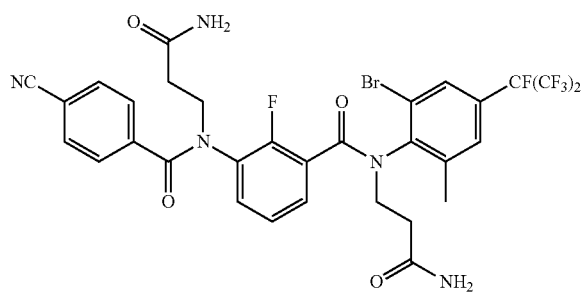
CK12

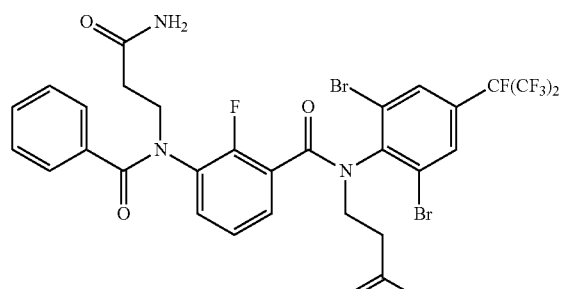
CK13

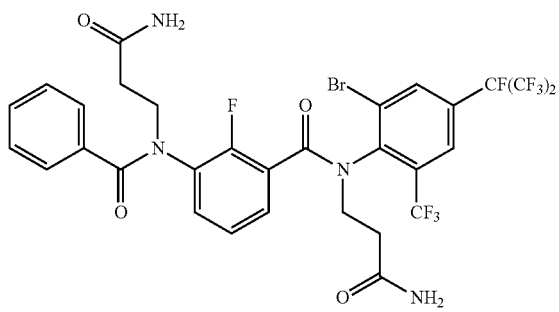
CK14

The patent CN102119144A discloses the following compound CK15 (compound No. 3-14), having certain insecticidal activity.

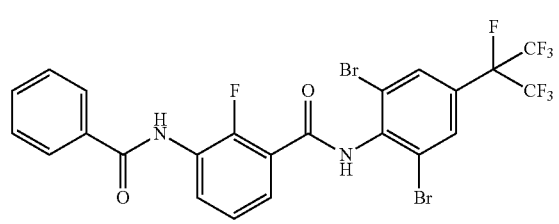
CK15

The patent CN102119143A discloses the following compound CK16 (compound No. 7-1574); the compound has certain insecticidal activity; moreover, the compound is, as an insecticide, being studied and developed, and its generic name is broflanilide.

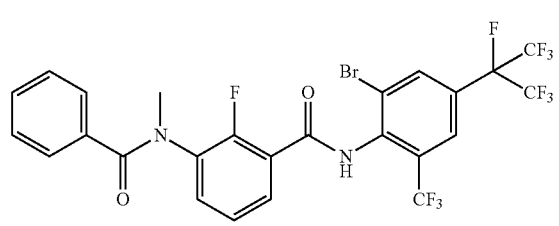
CK16

While there is no report on the compound shown in the Formula I and its insecticidal activity of the present invention in the prior art. Moreover, compared with the prior art, the compound of the present invention has higher insecticidal activity and more excellent fast-acting insecticidal efficacy.

SUMMARY OF THE INVENTION

The objective of the present invention is to provide a benzamide compound. The compound can be used in the preparation of a drug for controlling pests in agricultural and other fields.

The technical solution of present invention is as follows:
A benzamide compound, as shown in Formula I:

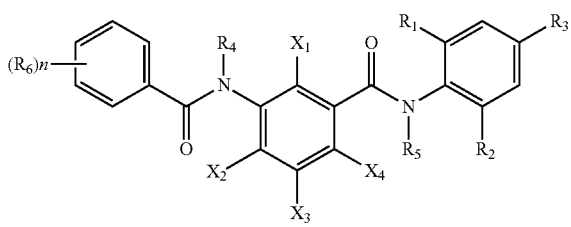

in the formula:

$R_1$ and $R_2$ are each independently selected from H, halogen, $C_1$-$C_6$ alkyl, $C_1$-$C_6$ haloalkyl, $C_1$-$C_6$ alkoxy or $C_1$-$C_6$ haloalkoxy;

$R_3$ is selected from heptafluoroisopropyl or nonafluoro-2-butyl;

$R_4$ and $R_5$ are each independently selected from H, $C_1$-$C_6$ alkyl, $C_1$-$C_6$ haloalkyl or cyanomethyl; moreover, at least one of $R_4$ and $R_5$ is selected from cyanomethyl;

$R_6$ is selected from H, halogen, cyano, nitryl, $C_1$-$C_6$ alkyl, $C_1$-$C_6$ haloalkyl, $C_1$-$C_6$ alkoxy or $C_1$-$C_6$ haloalkoxy; $C_1$-$C_6$ alkylthio or $C_1$-$C_6$ haloalkylthio; n=1, 2, 3, 4 or 5; when n is more than 1, $R_6$ can be the same or not the same.

$X_1$, $X_2$, $X_3$, and $X_4$ are each independently selected from H, halogen, cyano or $C_1$-$C_6$ alkoxy; moreover, $X_1$, $X_2$, $X_3$, and $X_4$ are not simultaneously H.

Preferably, the compound of the present invention is as follows: in the Formula I, $R_1$ and $R_2$ are each independently selected from H, halogen, $C_1$-$C_4$ alkyl, $C_1$-$C_4$ haloalkyl, $C_1$-$C_4$ alkoxy or $C_1$-$C_4$ haloalkoxy;

$R_3$ is selected from heptafluoroisopropyl or nonafluoro-2-butyl;

$R_4$ and $R_5$ are each independently selected from H, methyl, ethyl or cyanomethyl; moreover, at least one of $R_4$ and $R_5$ is selected from cyanomethyl;

$R_6$ is selected from H, halogen, cyano, nitryl, $C_1$-$C_4$ alkyl, $C_1$-$C_4$ haloalkyl, $C_1$-$C_4$ alkoxy or $C_1$-$C_4$ haloalkoxy; $C_1$-$C_4$ alkylthio or $C_1$-$C_4$ haloalkylthio; n=1, 2, 3, or 4;

$X_1$ is selected from F;

$X_2$, $X_3$, and $X_4$ are each independently selected from H, F or cyano.

More preferably, the compound of the present invention is as follows: in the Formula I, $R_1$ and $R_2$ are each independently selected from H, halogen, methyl, ethyl, trifluoromethyl or difluoromethoxy;

$R_3$ is selected from heptafluoroisopropyl or nonafluoro-2-butyl;

$R_4$ and $R_5$ are each independently selected from H, methyl, ethyl or cyanomethyl; moreover, at least one of $R_4$ and $R_5$ is selected from cyanomethyl;

$R_6$ is selected from H, F, Cl, Br, cyano, nitryl, methyl, ethyl, propyl, tertiary butyl, trifluoromethyl, heptafluoroisopropyl, methoxy or trifluoromethoxy; n=1, 2 or 3;

$X_1$ is selected from F;

$X_2$, $X_3$, and $X_4$ are each independently selected from H, or F.

Further preferably, the compound of the present invention is as follows: in the Formula I, $R_1$ and $R_2$ are each independently selected from H, halogen, methyl, ethyl, trifluoromethyl or difluoromethoxy;

$R_3$ is selected from heptafluoroisopropyl or nonafluoro-2-butyl;

$R_4$ is selected from cyanomethyl;

$R_5$ is selected from H, methyl, ethyl or cyanomethyl;

$R_6$ is selected from H, F, Cl, Br, cyano, nitryl, methyl, ethyl, propyl, tertiary butyl, trifluoromethyl, heptafluoroisopropyl, methoxy or trifluoromethoxy; n=1, 2 or 3;

$X_1$ is selected from F;

$X_2$, $X_3$, and $X_4$ are each independently selected from H, or F.

Or, further preferably, the compound of the present invention is as follows: in the Formula I, $R_1$ and $R_2$ are each independently selected from H, halogen, methyl, ethyl, trifluoromethyl or difluoromethoxy;

$R_3$ is selected from heptafluoroisopropyl or nonafluoro-2-butyl;

$R_4$ is selected from H, methyl, or ethyl;

$R_5$ is selected from cyanomethyl;

$R_6$ is selected from H, F, Cl, Br, cyano, nitryl, methyl, ethyl, propyl, tertiary butyl, trifluoromethyl, heptafluoroisopropyl, methoxy or trifluoromethoxy; n=1, 2 or 3;

$X_1$ is selected from F;

$X_2$, $X_3$, and $X_4$ are each independently selected from H, or F.

In the definition of the compound shown in the Formula I above, generally, the terms used herein represent the following substituents:

Halogen: F, Cl, Br or I.

Alkyl: linear or branched alkyl, such as methyl, ethyl, n-propyl, isopropyl or different butyl, amyl or hexyl isomers.

Haloalkyl: linear or branched alkyl; H atoms on these alkyls may be partly or totally substituted by halogen, such as chloromethyl, dichloromethyl, trichloromethyl, fluoromethyl, difluoromethyl, Trifluoromethyl, 2,2,2-trifluoroethyl, heptafluoroisopropyl

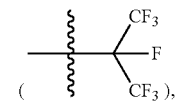

nonafluoro-2-butyl

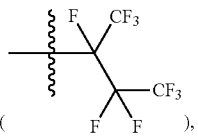

1,1,2,2,2-pentafluoroethyl.

Alkoxy: linear or branched alkyl, bond to a structure by an oxygen atomic bond, such as methoxy, ethoxy, tert-butoxy.

Haloalkoxy: H atoms on alkoxy may be partly or totally substituted by halogen, such as chloromethoxy, dichloromethoxy, trichloromethoxy, fluoromethoxy, difluoromethoxy, trifluoroethoxy, chlorofluoromethoxy, trifluoroethoxy.

Alkylthio: linear or branched alkyl, bond to a structure by a sulphur atomic bond, such as methylthio, ethylthio.

Haloalkylthio: H atoms on alkylthio may be partly or totally substituted by halogen, such as difluoromethylthio, trifluoroethylthio.

Cyanomethyl: $CNCH_2$—.

Partial compounds of the Formula I of the present invention are shown in tables 1-70, but the present invention is not limited to these compounds.

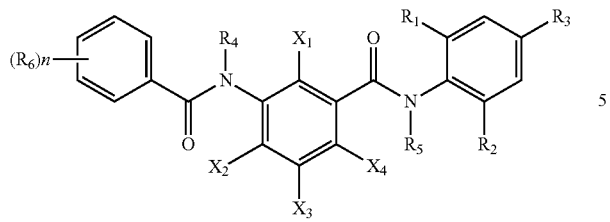

In the Formula I, when $R_1=R_2=CH_3$, $R_3$=heptafluoroisopropyl, $X_1$=F, $X_2=X_3=X_4$=H, $R_4$=cyanomethyl and $R_5$=H, $(R_6)_n$ is a different substituent as shown in table 1; and the compounds are represented by No. 1.1-1.321.

TABLE 1

| No. | $(R_6)n$ | No. | $(R_6)n$ | No. | $(R_6)n$ |
|---|---|---|---|---|---|
| 1.1 | 2-F | 1.2 | 2-Cl | 1.3 | 2-Br |
| 1.4 | 3-F | 1.5 | 3-Cl | 1.6 | 3-Br |
| 1.7 | 4-F | 1.8 | 4-Cl | 1.9 | 4-Br |
| 1.10 | 2-I | 1.11 | 2-CN | 1.12 | 2-NO$_2$ |
| 1.13 | 3-I | 1.14 | 3-CN | 1.15 | 3-NO$_2$ |
| 1.16 | 4-I | 1.17 | 4-CN | 1.18 | 4-NO$_2$ |
| 1.19 | 2-CH$_3$ | 1.20 | 2-C$_2$H$_5$ | 1.21 | 2-CH$_2$CH$_2$CH$_3$ |
| 1.22 | 3-CH$_3$ | 1.23 | 3-C$_2$H$_5$ | 1.24 | 3-CH$_2$CH$_2$CH$_3$ |
| 1.25 | 4-CH$_3$ | 1.26 | 4-C$_2$H$_5$ | 1.27 | 4-CH$_2$CH$_2$CH$_3$ |
| 1.28 | 2-CH(CH$_3$)$_2$ | 1.29 | 2-CH$_2$CH$_2$CH$_2$CH$_3$ | 1.30 | 2-C(CH$_3$)$_3$ |
| 1.31 | 3-CH(CH$_3$)$_2$ | 1.32 | 3-CH$_2$CH$_2$CH$_2$CH$_3$ | 1.33 | 3-C(CH$_3$)$_3$ |
| 1.34 | 4-CH(CH$_3$)$_2$ | 1.35 | 4-CH$_2$CH$_2$CH$_2$CH$_3$ | 1.36 | 4-C(CH$_3$)$_3$ |
| 1.37 | 2-CF$_3$ | 1.38 | 2-CF(CF$_3$)$_2$ | 1.39 | 2-OCH$_3$ |
| 1.40 | 3-CF$_3$ | 1.41 | 3-CF(CF$_3$)$_2$ | 1.42 | 3-OCH$_3$ |
| 1.43 | 4-CF$_3$ | 1.44 | 4-CF(CF$_3$)$_2$ | 1.45 | 4-OCH$_3$ |
| 1.46 | 2-OC$_2$H$_5$ | 1.47 | 2-OCF$_3$ | 1.48 | 2-OCHF$_2$ |
| 1.49 | 3-OC$_2$H$_5$ | 1.50 | 3-OCF$_3$ | 1.51 | 3-OCHF$_2$ |
| 1.52 | 4-OC$_2$H$_5$ | 1.53 | 4-OCF$_3$ | 1.54 | 4-OCHF$_2$ |
| 1.55 | 2-OCH$_2$CF$_3$ | 1.56 | 2-SCH$_3$ | 1.57 | 2-SCF$_3$ |
| 1.58 | 3-OCH$_2$CF$_3$ | 1.59 | 3-SCH$_3$ | 1.60 | 3-SCF$_3$ |
| 1.61 | 4-OCH$_2$CF$_3$ | 1.62 | 4-SCH$_3$ | 1.63 | 4-SCF$_3$ |
| 1.64 | 2,3-2F | 1.65 | 2,3-2Cl | 1.66 | 2,3-2Br |
| 1.67 | 2,4-2F | 1.68 | 2,4-2Cl | 1.69 | 2,4-2Br |
| 1.70 | 2,5-2F | 1.71 | 2,5-2Cl | 1.72 | 2,5-2Br |
| 1.73 | 2,6-2F | 1.74 | 2,6-2Cl | 1.75 | 2,6-2Br |
| 1.76 | 3,4-2F | 1.77 | 3,4-2Cl | 1.78 | 3,4-2Br |
| 1.79 | 3,5-2F | 1.80 | 3,5-2Cl | 1.81 | 3,5-2Br |
| 1.82 | 2,3-2CN | 1.83 | 2,3-2NO$_2$ | 1.84 | 2,3-2CH$_3$ |
| 1.85 | 2,4-2CN | 1.86 | 2,4-2NO$_2$ | 1.87 | 2,4-2CH$_3$ |
| 1.88 | 2,5-2CN | 1.89 | 2,5-2NO$_2$ | 1.90 | 2,5-2CH$_3$ |
| 1.91 | 2,6-2CN | 1.92 | 2,6-2NO$_2$ | 1.93 | 2,6-2CH$_3$ |
| 1.94 | 3,4-2CN | 1.95 | 3,4-2NO$_2$ | 1.96 | 3,4-2CH$_3$ |
| 1.97 | 3,5-2CN | 1.98 | 3,5-2NO$_2$ | 1.99 | 3,5-2CH$_3$ |
| 1.100 | 2,3-2C$_2$H$_5$ | 1.101 | 2,3-2(CH$_2$)$_2$CH$_3$ | 1.102 | 2,3-2CH(CH$_3$)$_2$ |
| 1.103 | 2,4-2C$_2$H$_5$ | 1.104 | 2,4-2(CH$_2$)$_2$CH$_3$ | 1.105 | 2,4-2CH(CH$_3$)$_2$ |
| 1.106 | 2,5-2C$_2$H$_5$ | 1.107 | 2,5-2(CH$_2$)$_2$CH$_3$ | 1.108 | 2,5-2CH(CH$_3$)$_2$ |
| 1.109 | 2,6-2C$_2$H$_5$ | 1.110 | 2,6-2(CH$_2$)$_2$CH$_3$ | 1.111 | 2,6-2CH(CH$_3$)$_2$ |
| 1.112 | 3,4-2C$_2$H$_5$ | 1.113 | 3,4-2(CH$_2$)$_2$CH$_3$ | 1.114 | 3,4-2CH(CH$_3$)$_2$ |
| 1.115 | 3,5-2C$_2$H$_5$ | 1.116 | 3,5-2(CH$_2$)$_2$CH$_3$ | 1.117 | 3,5-2CH(CH$_3$)$_2$ |
| 1.118 | 2,3-2C(CH$_3$)$_3$ | 1.119 | 2,3-2CF$_3$ | 1.120 | 2,3-2OCH$_3$ |
| 1.121 | 2,4-2C(CH$_3$)$_3$ | 1.122 | 2,4-2CF$_3$ | 1.123 | 2,4-2OCH$_3$ |
| 1.124 | 2,5-2C(CH$_3$)$_3$ | 1.125 | 2,5-2CF$_3$ | 1.126 | 2,5-2OCH$_3$ |
| 1.127 | 2,6-2C(CH$_3$)$_3$ | 1.128 | 2,6-2CF$_3$ | 1.129 | 2,6-2OCH$_3$ |
| 1.130 | 3,4-2C(CH$_3$)$_3$ | 1.131 | 3,4-2CF$_3$ | 1.132 | 3,4-2OCH$_3$ |
| 1.133 | 3,5-2C(CH$_3$)$_3$ | 1.134 | 3,5-2CF$_3$ | 1.135 | 3,5-2OCH$_3$ |
| 1.136 | 2,3-2OCF$_3$ | 1.137 | 2,3-2SCH$_3$ | 1.138 | 2,3-2SCF$_3$ |
| 1.139 | 2,4-2OCF$_3$ | 1.140 | 2,4-2SCH$_3$ | 1.141 | 2,4-2SCF$_3$ |
| 1.142 | 2,5-2OCF$_3$ | 1.143 | 2,5-2SCH$_3$ | 1.144 | 2,5-2SCF$_3$ |
| 1.145 | 2,6-2OCF$_3$ | 1.146 | 2,6-2SCH$_3$ | 1.147 | 2,6-2SCF$_3$ |
| 1.148 | 3,4-2OCF$_3$ | 1.149 | 3,4-2SCH$_3$ | 1.150 | 3,4-2SCF$_3$ |
| 1.151 | 3,5-2OCF$_3$ | 1.152 | 3,5-2SCH$_3$ | 1.153 | 3,5-2SCF$_3$ |
| 1.154 | 2-F-4-Cl | 1.155 | 2-F-4-Br | 1.156 | 2-F-4-I |
| 1.157 | 2-F-3-Cl | 1.158 | 2-F-5-Cl | 1.159 | 2-F-6-Cl |
| 1.160 | 3-F-2-Cl | 1.161 | 3-F-4-Cl | 1.162 | 3-F-5-Cl |
| 1.163 | 3-F-6-Cl | 1.164 | 4-F-2-Cl | 1.165 | 4-F-3-Cl |
| 1.166 | 2-Cl-4-Br | 1.167 | 2-Cl-4-I | 1.168 | 3-Cl-4-I |
| 1.169 | 4-Cl-2-Br | 1.170 | 2-CN-3-F | 1.171 | 2-CN-3-Cl |
| 1.172 | 2-CN-4-Cl | 1.173 | 2-CN-4-Br | 1.174 | 2-CN-4-NO$_2$ |

TABLE 1-continued

| No. | $(R_6)n$ | No. | $(R_6)n$ | No. | $(R_6)n$ |
|---|---|---|---|---|---|
| 1.175 | 4-CN-2-Cl | 1.176 | 4-CN-2-$CF_3$ | 1.177 | 4-CN-2-$NO_2$ |
| 1.178 | 2-$NO_2$-4-F | 1.179 | 2-$NO_2$-4-Cl | 1.180 | 2-$NO_2$-4-Br |
| 1.181 | 2-$NO_2$-4-$OCH_3$ | 1.182 | 2-$NO_2$-4-$OC_2H_5$ | 1.183 | 2-$NO_2$-5-Cl |
| 1.184 | 3-$NO_2$-4-F | 1.185 | 3-$NO_2$-4-Cl | 1.186 | 3-$NO_2$-4-Br |
| 1.187 | 4-$NO_2$-2-Cl | 1.188 | 4-$NO_2$-2-$OCH_3$ | 1.189 | 5-$NO_2$-2-F |
| 1.190 | 5-$NO_2$-2-Cl | 1.191 | 5-$NO_2$-2-Br | 1.192 | 5-$NO_2$-2-$OCH_3$ |
| 1.193 | 2-$CH_3$-4-F | 1.194 | 2-$CH_3$-4-Cl | 1.195 | 2-$CH_3$-4-Br |
| 1.196 | 2-$CH_3$-4-I | 1.197 | 2-$CH_3$-4-$NO_2$ | 1.198 | 2-$CH_3$-4-$OCH_3$ |
| 1.199 | 2-$CH_3$-3-F | 1.200 | 2-$CH_3$-3-Cl | 1.201 | 2-$CH_3$-3-$NO_2$ |
| 1.202 | 2-$CH_3$-5-F | 1.203 | 2-$CH_3$-5-Cl | 1.204 | 2-$CH_3$-5-Br |
| 1.205 | 2-$CH_3$-5-$NO_2$ | 1.206 | 2-$CH_3$-6-Cl | 1.207 | 2-CH3-6-$C_2H_5$ |
| 1.208 | 2-$CH_3$-6-$NO_2$ | 1.209 | 3-$CH_3$-2-Cl | 1.210 | 3-$CH_3$-2-Br |
| 1.211 | 3-$CH_3$-4-Cl | 1.212 | 3-$CH_3$-4-Br | 1.213 | 3-$CH_3$-4-I |
| 1.214 | 4-$CH_3$-2-Cl | 1.215 | 4-$CH_3$-3-Cl | 1.216 | 4-$CH_3$-2-Br |
| 1.217 | 4-$CH_3$-3-Br | 1.218 | 4-$CH_3$-3-F | 1.219 | 4-$CH_3$-2-$NO_2$ |
| 1.220 | 4-$CH_3$-3-$NO_2$ | 1.221 | 5-$CH_3$-2-F | 1.222 | 5-$CH_3$-2-CN |
| 1.223 | 5-$CH_3$-2-$OCH_3$ | 1.224 | 4-$C(CH_3)_3$-2-Cl | 1.225 | 2-$CF_3$-4-Cl |
| 1.226 | 2-$CF_3$-4-Br | 1.227 | 2-$CF_3$-4-$NO_2$ | 1.228 | 3-$CF_3$-4-F |
| 1.229 | 3-$CF_3$-4-Cl | 1.230 | 3-$CF_3$-4-$NO_2$ | 1.231 | 4-$CF_3$-2-Cl |
| 1.232 | 4-$CF_3$-2-Br | 1.233 | 4-$CF_3$-2-$NO_2$ | 1.234 | 5-$CF_3$-2-Cl |
| 1.235 | 5-$CF_3$-2-Br | 1.236 | 5-$CF_3$-2-$OCH_3$ | 1.237 | 2-$OCH_3$-5-Cl |
| 1.238 | 4-$OCH_3$-3-F | 1.239 | 4-$OCH_3$-3-Cl | 1.240 | 2-$OCF_3$-4-Cl |
| 1.241 | 2-$OCF_3$-4-Br | 1.242 | 2-$OCF_3$-4-CN | 1.243 | 4-$OCF_3$-2-Cl |
| 1.244 | 4-$OCF_3$-2-Br | 1.245 | 4-$OCF_3$-2-$NO_2$ | 1.246 | 2-$SCH_3$-5-Cl |
| 1.247 | 2,3,4-3F | 1.248 | 2,3,4-3Cl | 1.249 | 2,3,4-3Br |
| 1.250 | 2,3,5-3F | 1.251 | 2,3,5-3Cl | 1.252 | 2,3,5-3Br |
| 1.253 | 2,3,6-3F | 1.254 | 2,3,6-3Cl | 1.255 | 2,3,6-3Br |
| 1.256 | 2,4,5-3F | 1.257 | 2,4,5-3Cl | 1.258 | 2,4,5-3Br |
| 1.259 | 2,4,6-3F | 1.260 | 2,4,6-3Cl | 1.261 | 2,4,6-3Br |
| 1.262 | 3,4,5-3F | 1.263 | 3,4,5-3Cl | 1.264 | 3,4,5-3Br |
| 1.265 | 2,4,6-3$CH_3$ | 1.266 | 2,4,6-3$C_2H_5$ | 1.267 | 2,4,6-3$CH(CH_3)_2$ |
| 1.268 | 2,4,6-3$C(CH_3)_3$ | 1.269 | 2,4,6-3$CF_3$ | 1.270 | 2,4,6-3$NO_2$ |
| 1.271 | 2,4,6-3$OCH_3$ | 1.272 | 3,4,5-3$OCH_3$ | 1.273 | 2,4,6-3$OCF_3$ |
| 1.274 | 2,4,6-3$SCH_3$ | 1.275 | 2,4,6-3$SCF_3$ | 1.276 | 2-F-4,6-2Br |
| 1.277 | 2-F-4-Cl-6-Br | 1.278 | 4-F-2,6-2Br | 1.279 | 2,4-2F-6-Cl |
| 1.280 | 2,3-2Cl-4-Br | 1.281 | 2-$CH_3$-4,6-2Br | 1.282 | 3-$CH_3$-4,6-2Cl |
| 1.283 | 4-$CH_3$-2,6-2Br | 1.284 | 2,3-2$CH_3$-6-$NO_2$ | 1.285 | 4,5-2$CH_3$-2-$NO_2$ |
| 1.286 | 2,6-2$CH_3$-4-$C(CH_3)_3$ | 1.287 | 2-$CH_3$-4-$NO_2$-6-Cl | 1.288 | 2-$CH_3$-4-$NO_2$-6-Br |
| 1.289 | 2-$CH_3$-6-$NO_2$-4-Cl | 1.290 | 2-$CH_3$-6-$NO_2$-4-Br | 1.291 | 5-$CH_3$-4-F-6-Cl |
| 1.292 | 5-$CH_3$-2-$OCH_3$-4-Cl | 1.293 | 2-$CF_3$-4,6-2Cl | 1.294 | 2-$CF_3$-4,6-2Br |
| 1.295 | 4-$CF_3$-2,6-2Cl | 1.296 | 4-$CF_3$-2,6-2Br | 1.297 | 4-$CF_3$-2-$NO_2$-5-Cl |
| 1.298 | 4-$CF_3$-2-$NO_2$-6-Cl | 1.299 | 4-$CF_3$-2-$NO_2$-6-Br | 1.300 | 4-$CF_3$-2-Cl-6-Br |
| 1.301 | 2-$NO_2$-4,6-2Br | 1.302 | 2-$NO_2$-4-F-5-Cl | 1.303 | 4-$NO_2$-2,6-2Cl |
| 1.304 | 4-$NO_2$-2,6-2Br | 1.305 | 4-$NO_2$-2,5-2Cl | 1.306 | 2,4-2$NO_2$-6-Cl |
| 1.307 | 2,4-2$NO_2$-6-Br | 1.308 | 2-CN-4,6-2Cl | 1.309 | 2-CN-4,6-2Br |
| 1.310 | 4-CN-2,6-2Cl | 1.311 | 2-CN-4-$NO_2$-6-Cl | 1.312 | 2-CN-4-$NO_2$-6-Br |
| 1.313 | 2,5-2$OCH_3$-4-$NO_2$ | 1.314 | 2,4-2$OCH_3$-5-Cl | 1.315 | 2,3,5,6-4F |
| 1.316 | 4-F-3-Cl-2,6-2Br | 1.317 | 6-$NO_2$-2,3,4-3F | 1.318 | 2,3,4,5,6-5F |
| 1.319 | 2,3,4,5,6-5Cl | 1.320 | 2,3,5,6-4F-4-$CF_3$ | 1.321 | H |

Table 2: In the Formula I, when $R_1=R_2=Br$, $R_3$=heptafluoroisopropyl, $X_1=F$, $X_2=X_3=X_4=H$, $R_4$=cyanomethyl and $R_5=H$, $(R_6)_n$ is a different substituent consistent with table 1, successively corresponding to the substituents recorded in 1.1-1.321 of table 1; and the compounds are represented by No. 2.1-2.321.

Table 3: In the Formula I, when $R_1=R_2=Cl$, $R_3$=heptafluoroisopropyl, $X_1=F$, $X_2=X_3=X_4=H$, $R_4$=cyanomethyl and $R_5=H$, $(R_6)_n$ is a different substituent consistent with table 1, successively corresponding to the substituents recorded in 1.1-1.321 of table 1; and the compounds are represented by No. 3.1-3.321.

Table 4: In the Formula I, when $R_1=R_2=CF_3$, $R_3$=heptafluoroisopropyl, $X_1=F$, $X_2=X_3=X_4=H$, $R_4$=cyanomethyl and $R_5=H$, $(R_6)_n$ is a different substituent consistent with table 1, successively corresponding to the substituents recorded in 1.1-1.321 of table 1; and the compounds are represented by No. 4.1-4.321.

Table 5: In the Formula I, when $R_1=CH_3$, $R_2=CH_2CH_3$, $R_3$=heptafluoroisopropyl, $X_1=F$, $X_2=X_3=X_4=H$, $R_4$=cyanomethyl and $R_5=H$, $(R_6)_n$ is a different substituent consistent with table 1, successively corresponding to the substituents recorded in 1.1-1.321 of table 1, with the compounds are represented by No. 5.1-5.321.

Table 6: In the Formula I, when $R_1=Br$, $R_2=CH_3$, $R_3$=heptafluoroisopropyl, $X_1=F$, $X_2=X_3=X_4=H$, $R_4$=cyanomethyl and $R_5=H$, $(R_6)_n$ is a different substituent consistent with table 1, successively corresponding to the substituents recorded in 1.1-1.321 of table 1; and the compounds are represented by No. 6.1-6.321.

Table 7: In the Formula I, when $R_1=Br$, $R_2=Cl$, $R_3$=heptafluoroisopropyl, $X_1=F$, $X_2=X_3=X_4=H$, $R_4$=cyanomethyl and $R_5=H$, $(R_6)_n$ is a different substituent consistent with table 1, successively corresponding to the substituents recorded in 1.1-1.321 of table 1; and the compounds are represented by No. 7.1-7.321.

Table 8: In the Formula I, when $R_1=Br$, $R_2=I$, $R_3$=heptafluoroisopropyl, $X_1=F$, $X_2=X_3=X_4=H$, $R_4$=cyanomethyl and $R_5=H$, $(R_6)_n$ is a different substituent consistent with table 1, successively corresponding to the substituents recorded in 1.1-1.321 of table 1; and the compounds are represented by No. 8.1-8.321.

Table 9: In the Formula I, when $R_1=Br$, $R_2=CF_3$, $R_3$=heptafluoroisopropyl, $X_1=F$, $X_2=X_3=X_4=H$, $R_4$=cyanomethyl and $R_5$=H, $(R_6)_n$ is a different substituent consistent with table 1, successively corresponding to the substituents recorded in 1.1-1.321 of table 1; and the compounds are represented by No. 9.1-9.321.

Table 10: In the Formula I, when $R_1$=Cl, $R_2$=$CF_3$, $R_3$=heptafluoroisopropyl, $X_1$=F, $X_2$=$X_3$=$X_4$=H, $R_4$=cyanomethyl and $R_5$=H, $(R_6)_n$ is a different substituent consistent with table 1, successively corresponding to the substituents recorded in 1.1-1.321 of table 1; and the compounds are represented by No. 10.1-10.321.

Table 11: In the Formula I, when $R_1$=I, $R_2$=$CF_3$, $R_3$=heptafluoroisopropyl, $X_1$=F, $X_2$=$X_3$=$X_4$=H, $R_4$=cyanomethyl and $R_5$=H, $(R_6)_n$ is a different substituent consistent with table 1, successively corresponding to the substituents recorded in 1.1-1.321 of table 1; and the compounds are represented by No. 11.1-11.321.

Table 12: In the Formula I, when $R_1$=Br, $R_2$=$OCHF_2$, $R_3$=heptafluoroisopropyl, $X_1$=F, $X_2$=$X_3$=$X_4$=H, $R_4$=cyanomethyl and $R_5$=H, $(R_6)_n$ is a different substituent consistent with table 1, successively corresponding to the substituents recorded in 1.1-1.321 of table 1; and the compounds are represented by No. 12.1-12.321.

Table 13: In the Formula I, when $R_1$=Cl, $R_2$=$OCHF_2$, $R_3$=heptafluoroisopropyl, $X_1$=F, $X_2$=$X_3$=$X_4$=H, $R_4$=cyanomethyl and $R_5$=H, $(R_6)_n$ is a different substituent consistent with table 1, successively corresponding to the substituents recorded in 1.1-1.321 of table 1; and the compounds are represented by No. 13.1-13.321.

Table 14: In the Formula I, when $R_1$=I, $R_2$=$OCHF_2$, $R_3$=heptafluoroisopropyl, $X_1$=F, $X_2$=$X_3$=$X_4$=H, $R_4$=cyanomethyl and $R_5$=H, $(R_6)_n$ is a different substituent consistent with table 1, successively corresponding to the substituents recorded in 1.1-1.321 of table 1; and the compounds are represented by No. 14.1-14.321.

Table 15: In the Formula I, when $R_1$=$R_2$=$CH_3$, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 15.1-15.321.

Table 16: In the Formula I, when $R_1$=$R_2$=Br, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 16.1-16.321.

Table 17: In the Formula I, when $R_1$=$R_2$=Cl, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 17.1-17.321.

Table 18: In the Formula I, when $R_1$=$R_2$=$CF_3$, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 18.1-18.321.

Table 19: In the Formula I, when $R_1$=$CH_3$, $R_2$=$CH_2CH_3$, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 19.1-19.321.

Table 20: In the Formula I, when $R_1$=Br, $R_2$=$CH_3$, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 20.1-20.321.

Table 21: In the Formula I, when $R_1$=Br, $R_2$=Cl, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 21.1-21.321.

Table 22: In the Formula I, when $R_1$=Br, $R_2$=I, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 22.1-22.321.

Table 23: In the Formula I, when $R_1$=Br, $R_2$=$CF_3$, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 23.1-23.321.

Table 24: In the Formula I, when $R_1$=Cl, $R_2$=$CF_3$, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 24.1-24.321.

Table 25: In the Formula I, when $R_1$=I, $R_2$=$CF_3$, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 25.1-25.321.

Table 26: In the Formula I, when $R_1$=Br, $R_2$=$OCHF_2$, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 26.1-26.321.

Table 27: In the Formula I, when $R_1$=Cl, $R_2$=$OCHF_2$, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 27.1-27.321.

Table 28: In the Formula I, when $R_1$=I, $R_2$=$OCHF_2$, $R_3$=heptafluoroisopropyl, $X_1$=F, $X_2$=$X_3$=$X_4$=H, $R_4$=H and $R_5$=cyanomethyl, $(R_6)_n$ is a different substituent consistent with table 1, successively corresponding to the substituents recorded in 1.1-1.321 of table 1; and the compounds are represented by No. 28.1-28.321.

Table 29: In the Formula I, when $R_1$=$R_2$=$CH_3$, $R_3$=heptafluoroisopropyl, $X_1$=F, $X_2$=$X_3$=$X_4$=H, $R_4$=$CH_3$ and $R_5$=cyanomethyl, $(R_6)_n$ is a different substituent consistent with table 1, successively corresponding to the substituents recorded in 1.1-1.321 of table 1; and the compounds are represented by No. 29.1-29.321.

Table 30: In the Formula I, when $R_1$=$R_2$=Br, $R_3$=heptafluoroisopropyl, $X_1$=F, $X_2$=$X_3$=$X_4$=H, $R_4$=$CH_3$ and $R_5$=cyanomethyl, $(R_6)_n$ is a different substituent consistent with table 1, successively corresponding to the substituents recorded in 1.1-1.321 of table 1; and the compounds are represented by No. 30.1-30.321.

Table 31: In the Formula I, when $R_1$=$R_2$=Cl, $R_3$=heptafluoroisopropyl, $X_1$=F, $X_2$=$X_3$=$X_4$=H, $R_4$=$CH_3$ and $R_5$=cyanomethyl, $(R_6)_n$ is a different substituent consistent with table 1, successively corresponding to the substituents recorded in 1.1-1.321 of table 1; and the compounds are represented by No. 31.1-31.321.

Table 32: In the Formula I, when $R_1$=$R_2$=$CF_3$, $R_3$=heptafluoroisopropyl, $X_1$=F, $X_2$=$X_3$=$X_4$=H, $R_4$=$CH_3$ and $R_5$=cyanomethyl, $(R_6)_n$ is a different substituent consistent with table 1, successively corresponding to the substituents recorded in 1.1-1.321 of table 1; and the compounds are represented by No. 32.1-32.321.

Table 33: In the Formula I, when $R_1$=CH$_3$, $R_2$=CH$_2$CH$_3$, $R_3$=heptafluoroisopropyl, $X_1$=F, $X_2$=$X_3$=$X_4$=H, $R_4$=CH$_3$ and $R_5$=cyanomethyl, $(R_6)_n$ is a different substituent consistent with table 1, successively corresponding to the substituents recorded in 1.1-1.321 of table 1; and the compounds are represented by No. 33.1-33.321.

Table 34: In the Formula I, when $R_1$=Br, $R_2$=CH$_3$, $R_3$=heptafluoroisopropyl, $X_1$=F, $X_2$=$X_3$=$X_4$=H, $R_4$=CH$_3$ and $R_5$=cyanomethyl, $(R_6)_n$ is a different substituent consistent with table 1, successively corresponding to the substituents recorded in 1.1-1.321 of table 1; and the compounds are represented by No. 34.1-34.321.

Table 35: In the Formula I, when $R_1$=Br, $R_2$=Cl, $R_3$=heptafluoroisopropyl, $X_1$=F, $X_2$=$X_3$=$X_4$=H, $R_4$=CH$_3$ and $R_5$=cyanomethyl, $(R_6)_n$ is a different substituent consistent with table 1, successively corresponding to the substituents recorded in 1.1-1.321 of table 1; and the compounds are represented by No. 35.1-35.321.

Table 36: In the Formula I, when $R_1$=Br, $R_2$=I, $R_3$=heptafluoroisopropyl, $X_1$=F, $X_2$=$X_3$=$X_4$=H, $R_4$=CH$_3$ and $R_5$=cyanomethyl, $(R_6)_n$ is a different substituent consistent with table 1, successively corresponding to the substituents recorded in 1.1-1.321 of table 1; and the compounds are represented by No. 36.1-36.321.

Table 37: In the Formula I, when $R_1$=Br, $R_2$=CF$_3$, $R_3$=heptafluoroisopropyl, $X_1$=F, $X_2$=$X_3$=$X_4$=H, $R_4$=CH$_3$ and $R_5$=cyanomethyl, $(R_6)_n$ is a different substituent consistent with table 1, successively corresponding to the substituents recorded in 1.1-1.321 of table 1; and the compounds are represented by No. 37.1-37.321.

Table 38: In the Formula I, when $R_1$=Cl, $R_2$=CF$_3$, $R_3$=heptafluoroisopropyl, $X_1$=F, $X_2$=$X_3$=$X_4$=H, $R_4$=CH$_3$ and $R_5$=cyanomethyl, $(R_6)_n$ is a different substituent consistent with table 1, successively corresponding to the substituents recorded in 1.1-1.321 of table 1; and the compounds are represented by No. 38.1-38.321.

Table 39: In the Formula I, when $R_1$=I, $R_2$=CF$_3$, $R_3$=heptafluoroisopropyl, $X_1$=F, $X_2$=$X_3$=$X_4$=H, $R_4$=CH$_3$ and $R_5$=cyanomethyl, $(R_6)_n$ is a different substituent consistent with table 1, successively corresponding to the substituents recorded in 1.1-1.321 of table 1; and the compounds are represented by No. 39.1-39.321.

Table 40: In the Formula I, when $R_1$=Br, $R_2$=OCHF$_2$, $R_3$=heptafluoroisopropyl, $X_1$=F, $X_2$=$X_3$=$X_4$=H, $R_4$=CH$_3$ and $R_5$=cyanomethyl, $(R_6)_n$ is a different substituent consistent with table 1, successively corresponding to the substituents recorded in 1.1-1.321 of table 1; and the compounds are represented by No. 40.1-40.321.

Table 41: In the Formula I, when $R_1$=Cl, $R_2$=OCHF$_2$, $R_3$=heptafluoroisopropyl, $X_1$=F, $X_2$=$X_3$=$X_4$=H, $R_4$=CH$_3$ and $R_5$=cyanomethyl, $(R_6)_n$ is a different substituent consistent with table 1, successively corresponding to the substituents recorded in 1.1-1.321 of table 1; and the compounds are represented by No. 41.1-41.321.

Table 42: In the Formula I, when $R_1$=I, $R_2$=OCHF$_2$, $R_3$=heptafluoroisopropyl, $X_1$=F, $X_2$=$X_3$=$X_4$=H, $R_4$=CH$_3$ and $R_5$=cyanomethyl, $(R_6)_n$ is a different substituent consistent with table 1, successively corresponding to the substituents recorded in 1.1-1.321 of table 1; and the compounds are represented by No. 42.1-42.321.

Table 43: In the Formula I, when $R_1$=$R_2$=CH$_3$, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 43.1-43.321.

Table 44: In the Formula I, when $R_1$=$R_2$=Br, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent as shown in table 1, successively corresponding to the substituents recorded in 1.1-1.321 of table 1, and the compounds are represented by No. 44.1-44.321.

Table 45: In the Formula I, when $R_1$=$R_2$=Cl, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 45.1-45.321.

Table 46: In the Formula I, when $R_1$=$R_2$=CF$_3$, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 46.1-46.321.

Table 47: In the Formula I, when $R_1$=CH$_3$, $R_2$=CH$_2$CH$_3$, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 47.1-47.321.

Table 48: In the Formula I, when $R_1$=Br, $R_2$=CH$_3$, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 48.1-48.321.

Table 49: In the Formula I, when $R_1$=Br, $R_2$=Cl, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 49.1-49.321.

Table 50: In the Formula I, when $R_1$=Br, $R_2$=I, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent as shown in table 1, successively corresponding to the substituents recorded in 1.1-1.321 of table 1, and the compounds are represented by No. 50.1-50.321.

Table 51: In the Formula I, when $R_1$=Br, $R_2$=CF$_3$, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 51.1-51.321.

Table 52: In the Formula I, when $R_1$=Cl, $R_2$=CF$_3$, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 52.1-52.321.

Table 53: In the Formula I, when $R_1$=I, $R_2$=CF$_3$, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 53.1-53.321.

Table 54: In the Formula I, when $R_1$=Br, $R_2$=OCHF$_2$, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 54.1-54.321.

Table 55: In the Formula I, when $R_1$=Cl, $R_2$=OCHF$_2$, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 55.1-55.321.

Table 56: In the Formula I, when $R_1$=I, $R_2$=OCHF$_2$, $R_3$=heptafluoroisopropyl, $X_1$=F, $X_2$=$X_3$=$X_4$=H, $R_4$=cyanomethyl and $R_5$=CH$_3$, $(R_6)_n$ is a different substituent consistent with table 1, successively corresponding to the substituents recorded in 1.1-1.321 of table 1; and the compounds are represented by No. 56.1-56.321.

Table 57: In the Formula I, when $R_1$=$R_2$=CH$_3$, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 57.1-57.321.

Table 58: In the Formula I, when $R_1$=$R_2$=Br, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 58.1-58.321.

Table 59: In the Formula I, when $R_1$=$R_2$=Cl, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 59.1-59.321.

Table 60: In the Formula I, when $R_1$=$R_2$=CF$_3$, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 60.1-60.321.

Table 61: In the Formula I, when $R_1$=CH$_3$, $R_2$=CH$_2$CH$_3$, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 61.1-61.321.

Table 62: In the Formula I, when $R_1$=Br, $R_2$=CH$_3$, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 62.1-62.321.

Table 63: In the Formula I, when $R_1$=Br, $R_2$=Cl, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 63.1-63.321.

Table 64: In the Formula I, when $R_1$=Br, $R_2$=I, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 64.1-64.321.

Table 65: In the Formula I, when $R_1$=Br, $R_2$=CF$_3$, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 65.1-65.321.

Table 66: In the Formula I, when $R_1$=Cl, $R_2$=CF$_3$, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 66.1-66.321.

Table 67: In the Formula I, when $R_1$=I, $R_2$=CF$_3$, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 67.1-67.321.

Table 68: In the Formula I, when $R_1$=Br, $R_2$=OCHF$_2$, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 68.1-68.321.

Table 69: In the Formula I, when $R_1$=Cl, $R_2$=OCHF$_2$, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 69.1-69.321.

Table 70: In the Formula I, when $R_1$=I, $R_2$=OCHF$_2$, $R_3$=heptafluoroisopropyl, $X_1$=F, $X_2$=$X_3$=$X_4$=H and $R_4$=$R_5$=cyanomethyl, $(R_6)_n$ is a different substituent consistent with table 1, successively corresponding to the substituents recorded in 1.1-1.321 of table 1; and the compounds are represented by No. 70.1-70.321.

The compound of the Formula I of the present invention can be prepared by the following method (in the Formula, unless otherwise specified, the definition of each group is the same as the above; and LG=Cl or Br):

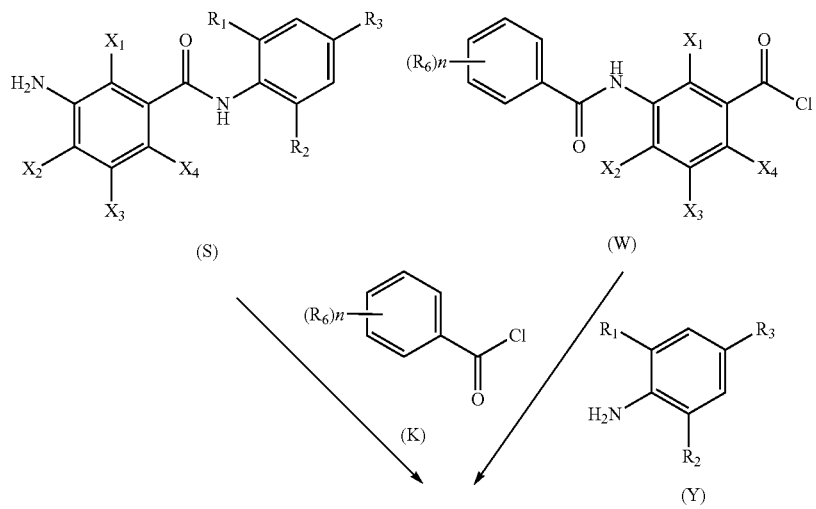

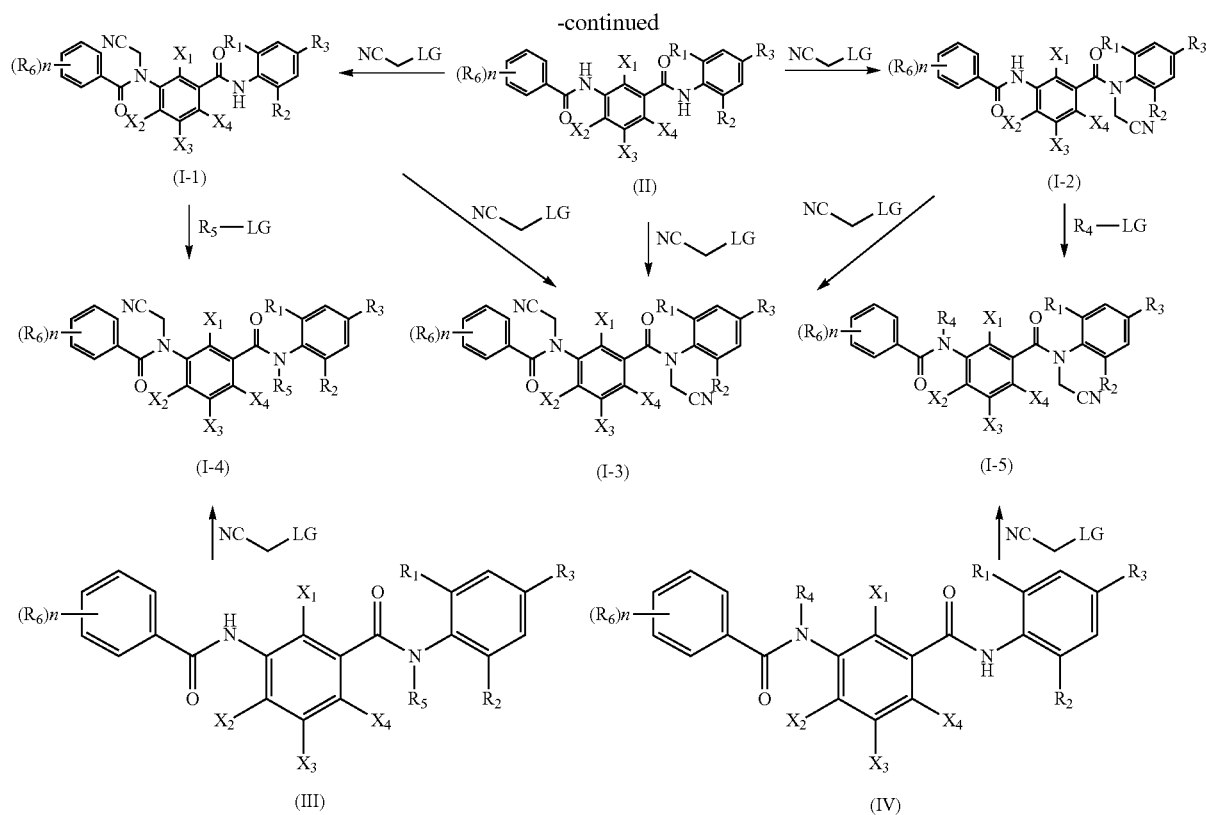

A compound of Formula S and a compound of Formula K, or a compound of Formula W and a compound of Formula Y react with each other in a proper solvent at the temperature from −10° C. to the boiling point of the solvent for 0.5-48 h to prepare a compound of Formula II; and the reaction may be conducted in the presence of alkali.

The compound of Formula II reacts with haloacetonitrile in the presence of a proper solvent and alkali at the temperature from −10° C. to the boiling point of the solvent for 0.5-48 h to respectively prepare compounds of Formulas I-1, I-2 and I-3. The compound of Formula 1 or 2 reacts with haloacetonitrile in the presence of a proper solvent and alkali at the temperature from −10° C. to the boiling point of the solvent for 0.5-48 h to prepare the compound of Formula I-3. The compound of Formula I-1 and a compound of Formula $R_5$-LG react with each other in the presence of a proper solvent and alkali at the temperature from −10° C. to the boiling point of the solvent for 0.5-48 h to prepare a compound of Formula I-4. The compound of Formula I-2 reacts with a compound of $R_4$-LG in the presence of a proper solvent and alkali at the temperature from −10° C. to the boiling point of the solvent for 0.5-48 h to prepare a compound of Formula I-5. A compound of Formula III ($R_5$ is merely a $C_1$-$C_6$ alkyl or $C_1$-$C_6$ haloalkyl) reacts with haloacetonitrile in the presence of a proper solvent and alkali at the temperature from −10° C. to the boiling point of the solvent for 0.5-48 h to prepare the compound of Formula I-4. A compound of Formula IV ($R_4$ is merely a $C_1$-$C_6$ alkyl or $C_1$-$C_6$ haloalkyl) reacts with haloacetonitrile in the presence of a proper solvent and alkali at the temperature from −10° C. to the boiling point of the solvent for 0.5-48 h to respectively prepare the compound of Formula I-5.

The above proper solvent may be selected from aromatic hydrocarbons such as benzene, methylbenzene and xylene, ketones such as acetone, methyl ethyl ketone and methyl isobutyl ketone, halohydrocarbons such as chloroform and dichloromethane, esters such as methyl acetate and ethyl acetate, ethers such as tetrahydrofuran, dioxane, diethyl ether and 1,2-dimethoxyethane, polar solvents such as water, acetonitrile, N, N-dimethylformamide, N-methyl pyrrolidone and dimethyl sulfoxide or a mixture of the above solvents. The proper alkali may be selected from organic alkalis such as triethylamine, pyridine, DBU, 4-dimethylamiopryidine, alkali metal hydrides such as sodium hydride and potassium hydride, alkali metal hydroxides such as sodium hydroxide and potassium hydroxide, alkali-earth metal hydroxides such as calcium hydroxide, alkali carbonate such as sodium carbonate and potassium carbonate, alkali metal bicarbonates such as sodium bicarbonate, and metal alkoxides such as sodium methylate, sodium ethoxide, potassium ethoxide, potassium tert-butoxide and sodium tert-butoxide.

The compounds of Formula $R_4$-LG Formula $R_5$-LG Formula K and Formula $CNCH_2$-LG as well as alkali are usually commercially available, and also may be prepared according to a conventional method. The compounds of Formula S, Formula W, Formula Y, Formula II, Formula III and Formula IV may be prepared according to a common general method, for example, prepared according to the methods recorded in WO2011093415, US20110201687, WO2005021488, WO2005073165, WO2010018857, WO2006137395, JP2007099761, WO2008000438, WO2008074427, WO2008107091, WO2010013567, WO2010018714, WO2010090282, WO2010127926, WO2010127928, JP2011063549, WO2012020483, WO2012020484, WO2012077221, WO2012164698, WO2013050261, WO2014069665, WO2014067838, WO2014161848, WO2014161850, WO2015097091 or WO2015097094.

The compound of Formula I of the present invention has unexpectedly high insecticidal activity, and can be used to control the following pests (the objects listed merely serve to specify the present invention, but are not to define the present invention): lepidoptera pests, such as, Plutella xylostella, armyworm, beet armyworm, prodenia litura, tobacco budworm, cabbage looper, Chilo suppressalis, tryporyza incertulas, rice leaf roller, Ostrinia nubilalis, grapholtitha molesta busck, cotton bollworm; homopteran pests, such as, pea aphid, bean aphid, beet aphid, cotton aphid, apple aphid, green peach aphid, corn leaf aphid, aleyrodid, leafhopper, plant hopper, rice planthopper and mealybug; hemiptera pests, such as maize chinch bug, cotton lace bug, cyrtopeltis modesta distant, Nezara viridula and rice stink bug; thysanoptera pests, such as Thrips tabaci, frankliniella occidentalis and Thrips nigropilosus uzel; coleoptera pests, such as potato beetle, elateridae, clitea metallica chen, leaf miner and sympiezomias velatus chevrolat; diptera pests, such as flies and mosquitos; hymenoptera pests, such as bees and ants. The compound of Formula I of the present invention further has unexpectedly high fast-acting insecticidal efficacy, and takes effect rapidly; moreover, the compound of the Formula I can achieve higher insecticidal activity 1 day after application, and extremely high insecticidal activity within 3 days. The compound of Formula I of the present invention has simple and efficient preparation method, facilitaets large-scale industrial production, and thus has extensive application prospects. Therefore, the technical solution of the present invention further includes a use of the compound of the Formula I in the preparation of an insecticide in agriculture and other fields.

Due to its positive property, the above compound can be advantageously used to protect important crops, livestock and breeding stock in agriculture and horticulture as well as the surroundings where people haunt about from being damaged by the pests.

To achieve an ideal effect, the dosage of the above compound varies from different factors, for example, the compound used, crops to be protected, type of pests, gradient of infection, weather conditions, application method, dosage forms taken, etc.

The compound at a dose of 10 g to 5 kg per hectare can take sufficient control effect.

The present invention further includes an insecticidal composition with the compound of Formula I as an active component. The weight percentage of the active component in the insecticidal composition is within 0.1-99%. The insecticidal composition further includes a carrier acceptable in agriculture, forestry and health.

The composition of the present invention can be applied in the form of formulations. The compound of the Formula I, as an active component, is dissolved or dispersed into a carrier or formulated into formulations so that it is easier to be dispersed when used as an insecticide. For example: these chemical formulations can be made into wettable powder, an oil suspension, a suspension concentrate, EW (emulsion in water), a water aqua or missible oil, etc. At least one kind of liquid or a solid carrier is added to these compositions, and moreover, a proper surfactant may be added when needed.

The technical solution of the present invention further includes a method for controlling pests: the insecticidal composition of the present invention is applied to the pests or a growth medium thereof. Usually, a more appropriately effective dose selected is from 10 g to 1000 g per hectare; preferably, the effective dose is from 10 g to 500 g per hectare.

For some application, for example, one or more other bactericides, pesticides/acaricide, herbicides, plant growth regulators or fertilizers, etc. can be added to the insecticidal composition of the present invention in agriculture, thus bringing additional advantages and effects.

It should be made clear that various transformations and alterations can be made within the scope set forth in the claims of the present invention.

DETAILED DESCRIPTION OF THE INVENTION

The present invention is further described by the following detailed embodiments, but the present invention is not limited to these examples. (Unless otherwise specified, the raw materials used are commercially available)

EXAMPLES OF SYNTHESIS

The compound of Formula I of the present invention may be prepared respectively with different raw materials based on the synthetic route described above; and the further detailed description is as follows:

Example 1: Preparation of Compound 2.321

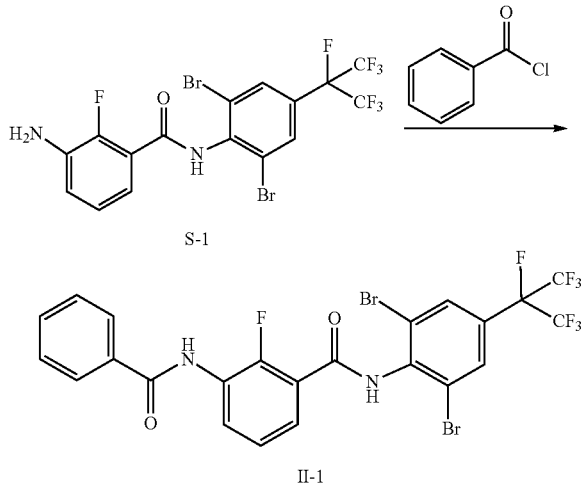

(1) Preparation of 3-benzamido-N-(2,6-dibromo-4-heptafluoroisopropylphenyl)-2-fluorobenzamide (intermediate II-1)

1.00 g (1.80 mmol) N-(2,6-dibromo-4-heptafluoroisopropylphenyl)-2-fluoro-3-aminobenzamide (intermediate S-1, prepared by reference to the methods disclosed in WO2010013567, WO02010018714, US20110201687 or WO2011093415, etc.) and 0.27 g (1.93 mmol) benzoyl chloride were added to 30 ml methylbenzene, and heating was performed for reflux. By TLC monitoring, and at the end of the reaction, the above solution was desolventized under reduced pressure; and then residuals were purified by column chromatography (eluent was ethyl acetate and petroleum ether with the volume ratio of 1:6-1:2) to obtain 1.09 g white solid, namely, the intermediate II-1.

(2) Preparation of compound 2.321

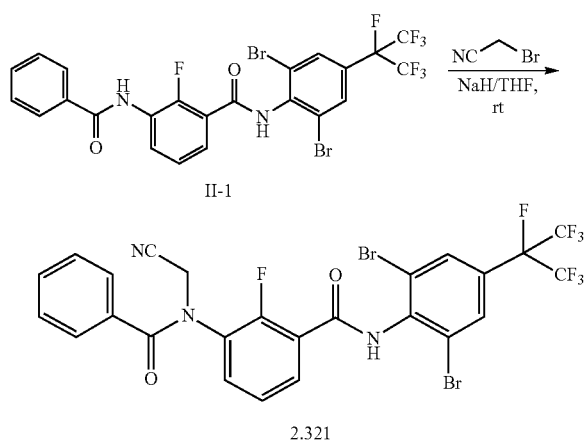

II-1

2.321

0.30 g (7.5 mmol) 60% sodium hydride was added to 10 ml tetrahydrofuran, 0.50 g (0.75 mmol) 3-benzamido-N-(2, 6-dibromo-4-heptafluoroisopropylphenyl)-2-fluorobenzamide (intermediate II-1) dissolved in 10 ml tetrahydrofuran was dropped in at room temperature, and then stirring was carried out for 10 min at room temperature; and 0.45 g (3.78 mmol) bromoacetonitrile was added and stirring was continued for 1 h at room temperature. By TLC monitoring, and at the end of the reaction, the reaction was quenched by ice water; ethyl acetate was added for extraction; an obtained product was dried by anhydrous magnesium sulfate, filtered, and desolventized under reduced pressure; and residuals were purified by column chromatography (eluent was ethyl acetate and petroleum ether with the volume ratio of 1:6-1:2) to obtain 0.38 g white solid.

The nuclear magnetism and mass spectrometric data of the compound 2.321 were as follows:

$^1$H NMR (600 MHz, internal standard TMS, solvent CDCl$_3$) δ (ppm): 8.10 (t, 1H), 7.98 (d, 1H), 7.86 (s, 2H), 7.54-7.48(m, 1H), 7.41-7.29 (m, 4H), 7.28-7.21(m, 2H), 4.80 (d, 2H).

$^1$H NMR (600 MHz, internal standard TMS, solvent DMSO) δ (ppm): 10.62 (d, 1H), 8.04 (d, 2H), 7.66 (d, 2H), 7.44-7.27 (m, 6H), 4.93 (s, 2H).

LC-MS(m/z): 722.0 (m+Na+H).

Similarly, the compounds 2.7, 2.17 and 2.43 were prepared according to the method of Example 1.

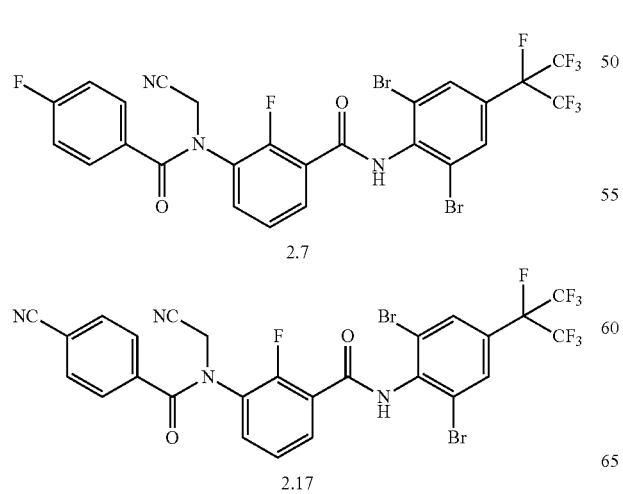

2.7

2.17

2.43

The nuclear magnetism and mass spectrometric data of the compound 2.7 were as follows:

$^1$H NMR (600 MHz, internal standard TMS, solvent CDCl$_3$) δ (ppm): 8.13 (t, 1H), 7.95 (d, 1H), 7.87 (s, 2H), 7.54-7.49 (m, 1H), 7.44-7.39 (m, 2H), 7.35 (t, 1H), 6.95 (t, 2H), 4.79 (d, 2H).

$^1$H NMR (600 MHz, internal standard TMS, solvent DMSO) δ (ppm): 10.62 (s, 1H), 8.04 (s, 2H), 7.73-7.65 (m, 2H), 7.48-7.42 (m, 2H), 7.38 (t, 1H), 7.15 (t, 2H), 4.94 (s, 2H).

LC-MS(m/z): 718.1 (m+H).

The nuclear magnetism and mass spectrometric data of the compound 2.17 were as follows:

$^1$H NMR (600 MHz, internal standard TMS, solvent CDCl$_3$) δ (ppm): 8.16 (t, 1H), 7.88 (s, 2H), 7.57 (d, 2H), 7.53-7.48 (m, 3H), 7.37 (t, 1H), 7.34 (s, 1H), 4.99 (s, 1H), 4.67 (s, 1H).

$^1$H NMR (600 MHz, internal standard TMS, solvent DMSO) δ (ppm): 10.59 (s, 1H), 8.04 (s, 2H), 7.80 (d, 2H), 7.77-7.67 (m, 2H), 7.55 (d, 2H), 7.38 (t, 1H), 4.99 (s, 2H).

LC-MS(m/z): 725.2 (m+H).

The nuclear magnetism and mass spectrometric data of the compound 2.43 were as follows:

$^1$H NMR (600 MHz, internal standard TMS, solvent CDCl$_3$) δ (ppm): 7.90-7.80 (m, 4H), 7.55 (d, 2H), 7.23 (s, 1H), 7.11 (s, 1H), 6.85 (s, 1H), 4.39-4.31 (m, 1H), 4.08 (d, 2H).

LC-MS(m/z): 767.9 (m+H).

Example 2: Preparation of Compound 3.321

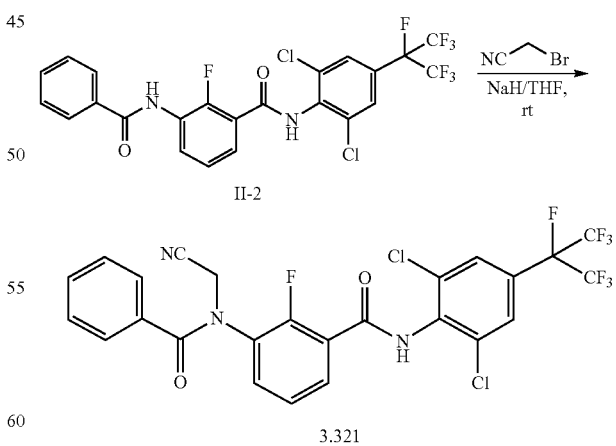

II-2

3.321

The method of preparing the compound 3.321 by 3-benzamido-N-(2, 6-dichloro-4-heptafluoroisopropylphenyl)-2-fluorobenzamide (intermediate II-2, prepared by reference to the method disclosed in WO2010018857) is the same as that of Example 1.

The nuclear magnetism and mass spectrometric data of the compound 3.321 were as follows:

¹H NMR (600 MHz, internal standard TMS, solvent CDCl₃) δ (ppm): 8.10 (t, 1H), 7.95 (d, 1H), 7.67 (s, 2H), 7.49 (t, 1H), 7.41-7.34 (m, 3H), 7.31 (t, 1H), 7.29-7.22 (m, 2H), 4.80 (d, 2H).

¹H NMR (600 MHz, internal standard TMS, solvent DMSO) δ (ppm): 10.61 (s, 1H), 7.92 (s, 2H), 7.70-7.58 (m, 2H), 7.42-7.27 (m, 6H), 4.93 (s, 2H).

LC-MS(m/z): 610.0 (m+H).

Example 3: Preparation of Compound 6.321

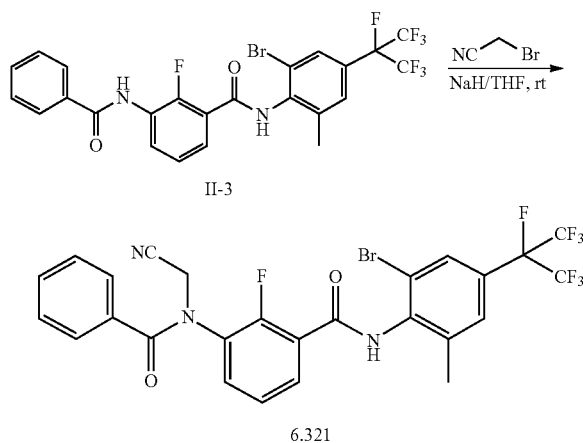

The method of preparing the compound 6.321 by 3-benzamido-N-(2-bromo-6-methyl-4-heptafluoroisopropylphenyl)-2-fluorobenzamide (intermediate II-3, prepared by reference to the method disclosed in WO2010018857) is the same as that of Example 1.

The nuclear magnetism and mass spectrometric data of the compound 6.321 were as follows:

¹H NMR (600 MHz, internal standard TMS, solvent CDCl₃) δ (ppm): 8.12-8.06 (m, 1H), 7.90 (d, 1H), 7.72 (s, 1H), 7.51 (t, 1H), 7.51 (t, 1H), 7.48 (s, 1H), 7.42-7.30 (m, 4H), 7.28-7.22 (m, 1H), 4.81 (d, 2H), 2.38 (s, 3H).

¹H NMR (600 MHz, internal standard TMS, solvent DMSO) δ (ppm): 10.29 (s, 1H), 7.80 (d, 1H), 7.70-7.64 (m, 2H), 7.59 (t, 1H), 7.38 (d, 3H), 7.35-7.27 (m, 3H), 4.93 (s, 2H), 2.35 (s, 3H).

LC-MS(m/z): 634.0 (m+H).

Example 4: Preparation of Compound 7.321

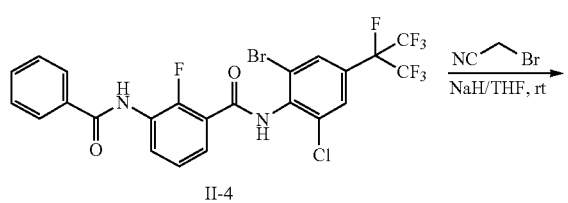

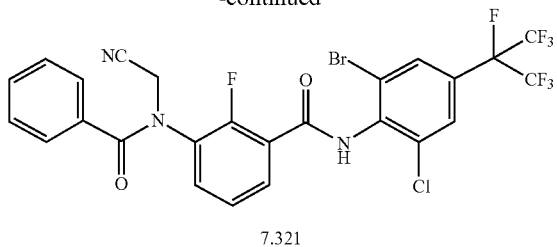

The method of preparing the compound 7.321 by 3-benzamido-N-(2-bromo-6-chloro-4-heptafluoroisopropylphenyl)-2-fluorobenzamide (intermediate II-4, prepared by reference to the method disclosed in WO2014161849) is the same as that of Example 1.

The nuclear magnetism and mass spectrometric data of the compound 7.321 were as follows:

¹H NMR (600 MHz, internal standard TMS, solvent CDCl₃) δ (ppm): 8.10 (t, 1H), 7.96 (d, 1H), 7.88-7.80 (m, 1H), 7.71 (d, 1H), 7.54-7.46 (m, 1H), 7.42-7.29 (m, 4H), 7.28-7.21 (m, 2H), 4.80 (d, 2H).

¹H NMR (600 MHz, internal standard TMS, solvent DMSO) δ (ppm): 10.61 (s, 1H), 8.05-7.99 (m, 1H), 7.95 (s, 1H), 7.71-7.58 (m, 2H), 7.42-7.27 (m, 6H), 4.93 (s, 2H).

LC-MS(m/z): 654.0 (m+H).

Example 5: Preparation of Compound 8.321

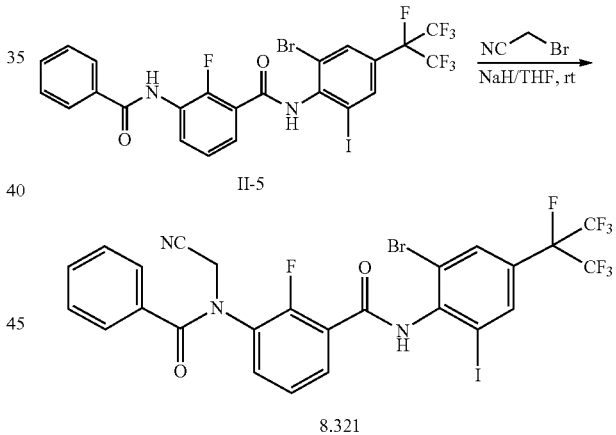

The method of preparing the compound 8.321 by 3-benzamido-N-(2-bromo-6-iodo-4-heptafluoroisopropylphenyl)-2-fluorobenzamide (intermediate II-5, prepared by reference to the method disclosed in WO2010018857) is the same as that of Example 1.

The nuclear magnetism and mass spectrometric data of the compound 8.321 were as follows:

¹H NMR (600 MHz, internal standard TMS, solvent CDCl₃) δ (ppm): 8.12 (t, 1H), 8.06 (d, 1H), 7.96 (d, 1H), 7.89 (d, 1H), 7.54 (t, 1H), 7.42-7.31 (m, 4H), 7.28-7.21 (m, 2H), 4.81 (d, 2H).

¹H NMR (600 MHz, internal standard TMS, solvent DMSO) δ (ppm): 10.61 (s, 1H), 8.14 (s, 1H), 8.02 (s, 1H), 7.70 (t, 1H), 7.66-7.60 (m, 1H), 7.41-7.28 (m, 6H), 4.93 (s, 2H).

LC-MS(m/z): 745.9 (m+H).

Example 6: Preparation of Compound 9.321

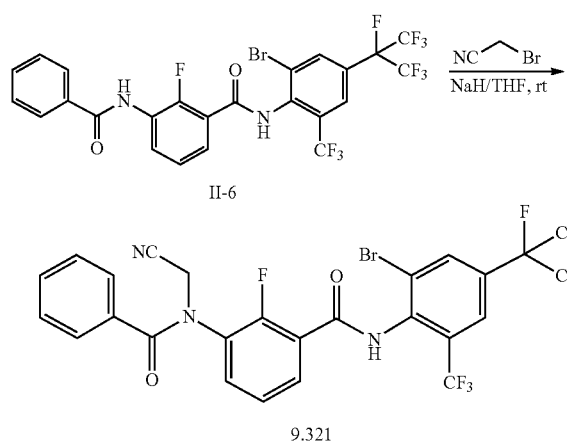

The method of preparing the compound 9.321 by 3-benzamido-N-(2-bromo-6-trifluoromethyl-4-heptafluoroisopropylphenyl)-2-fluorobenzamide (intermediate II-6, prepared by reference to the methods disclosed in WO2010013567, WO2010018714, US20110201687 or WO2011093415, etc.) is the same as that of Example 1.

The nuclear magnetism and mass spectrometric data of the compound 9.321 were as follows:

$^1$H NMR (600 MHz, internal standard TMS, solvent CDCl$_3$) δ (ppm): 8.13 (s, 1H), 8.08 (t, 1H), 8.03 (d, 1H), 7.91 (s, 1H), 7.53 (t, 1H), 7.40-7.30 (m, 4H), 7.28-7.22 (m, 2H), 4.80 (d, 2H).

$^1$H NMR (600 MHz, internal standard TMS, solvent DMSO) δ (ppm): 10.66 (s, 1H), 8.40 (d, 1H), 7.94 (d, 1H), 7.62 (q, 2H), 7.39-7.31 (m, 4H), 7.28 (t, 2H), 4.91 (s, 2H).

LC-MS(m/z): 687.9 (m+H).

Example 7: Preparation of Compound 16.321

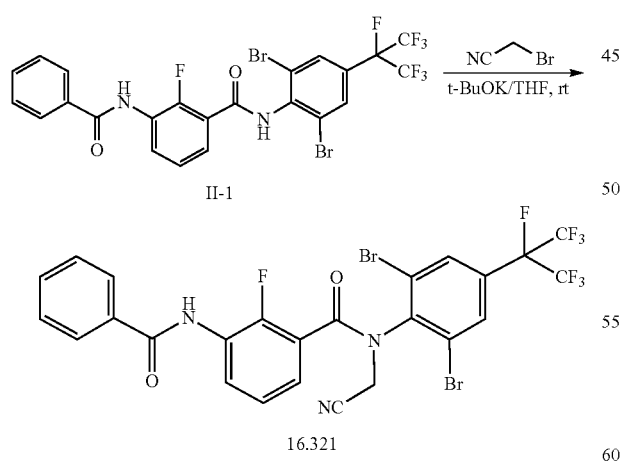

0.5 g (0.75 mmol) 3-benzamido-N-(2,6-dibromo-4-heptafluoroisopropylphenyl)-2-fluorobenzamide (intermediate II-1), 0.18 g (1.51 mmol) bromoacetonitrile, and 0.17 g (1.52 mmol) potassium tert-butoxide were added to 20 ml tetrahydrofuran, and then stirred for 5 h at room temperature. By TLC monitoring, and at the end of the reaction, water and ethyl acetate were added for extraction; an obtained product was dried by anhydrous magnesium sulfate, filtered, and desolventized under reduced pressure; residuals were purified by column chromatography (eluent was ethyl acetate and petroleum ether with the volume ratio of 1:6-1:2) to obtain 0.29 g white solid.

The nuclear magnetism and mass spectrometric data of the compound 16.321 were as follows:

$^1$H NMR (600 MHz, internal standard TMS, solvent CDCl$_3$) δ (ppm): 8.52 (td, 1H), 8.08 (s, 1H), 7.88-7.83 (m, 2H), 7.79 (s, 2H), 7.62-7.57 (m, 1H), 7.54-7.50 (m, 2H), 6.98-6.93 (m, 1H), 6.92-6.88 (m, 1H), 4.72 (s, 2H). LC-MS (m/z): 699.9 (m+H).

Similarly, the compounds 17.321, 20.321 and 21.321 were prepared according to the method of Example 7.

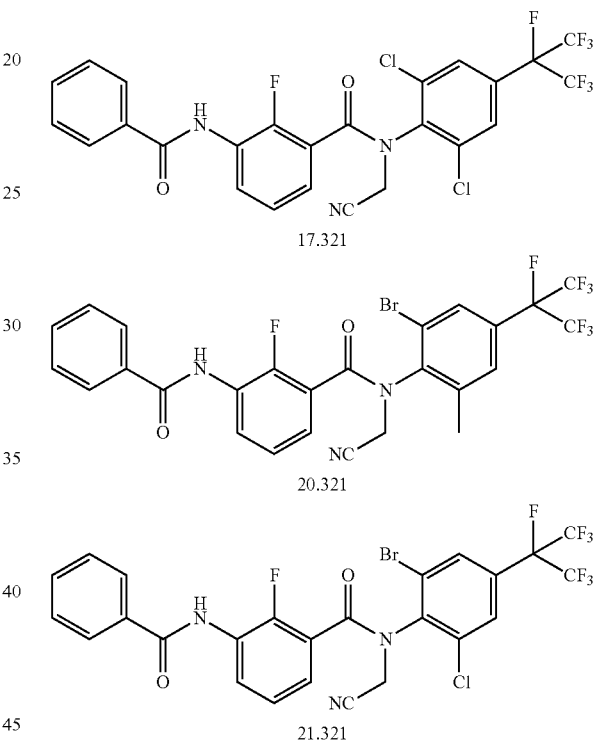

The nuclear magnetism and mass spectrometric data of the compound 17.321 were as follows:

$^1$H NMR (600 MHz, internal standard TMS, solvent CDCl$_3$) δ (ppm): 8.54-8.48 (m, 1H), 8.04 (d, 1H), 7.87-7.82 (m, 2H), 7.60-7.57 (m, 3H), 7.54-7.50 (m, 2H), 6.97 (t, 1H), 6.92-6.87 (m, 1H), 4.74 (s, 2H). LC-MS(m/z): 610.0 (m+H).

The nuclear magnetism and mass spectrometric data of the compound 20.321 were as follows:

$^1$H NMR (600 MHz, internal standard TMS, solvent CDCl$_3$) δ (ppm): 8.51-8.45 (m, 1H), 8.00 (d, 1H), 7.87-7.82 (m, 2H), 7.71 (s, 1H), 7.62-7.58 (m, 1H), 7.54-7.50 (m, 2H), 7.37 (s, 1H), 6.97 (t, 1H), 6.93-6.89 (m, 1H), 5.14 (d, 1H), 4.35 (d, 1H), 2.43 (s, 3H). LC-MS(m/z): 634.0 (m+H).

The nuclear magnetism and mass spectrometric data of the compound 21.321 were as follows: $^1$H NMR (600 MHz, internal standard TMS, solvent CDCl$_3$) δ (ppm): 8.56-8.50 (m, 1H), 8.05 (s, 1H), 7.88-7.83 (m, 2H), 7.76 (d, 1H), 7.64-7.58 (m, 2H), 7.56-7.50 (m, 2H), 6.97 (t, 1H), 6.93-6.87 (m, 1H), 4.79 (d, 1H), 4.68 (d, 1H). LC-MS(m/z): 654.0 (m+H).

Example 8: Preparation of Compound 30.321

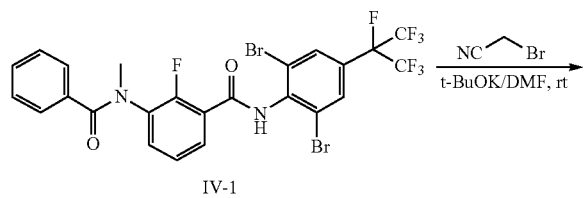

IV-1

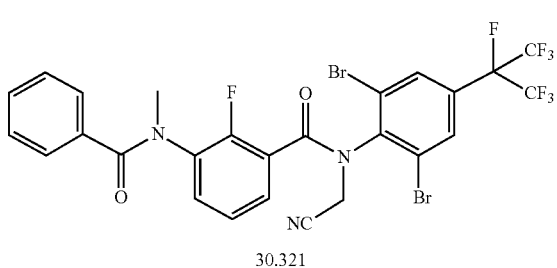

30.321

0.5 g (0.74 mmol) N-(2,6-dibromo-4-heptafluoroisopropylphenyl)-2-fluoro-3-(N-benzamido) benzamide (intermediate IV-1, prepared by reference to the methods disclosed in WO2010013567, WO2010018714, US20110201687 or WO2011093415, etc.), 0.18 g (1.51 mmol) bromoacetonitrile and 0.17 g (1.52 mmol) potassium tert-butoxide were added to 20 ml DMF, and then stirred at room temperature for 10 h. By TLC monitoring, and at the end of the reaction, water and ethyl acetate were added for extraction; an obtained product was dried by anhydrous magnesium sulfate, filtered, and desolventized under reduced pressure; and residuals were purified by column chromatography (eluent was ethyl acetate and petroleum ether with the volume ratio of 1:6-1:2) to obtain 0.34 g white solid.

The nuclear magnetism and mass spectrometric data of the compound 30.321 were as follows:

$^1$H NMR (600 MHz, internal standard TMS, solvent CDCl$_3$) δ (ppm): 7.76 (s, 2H), 7.49-7.37 (m, 1H), 7.28-7.21 (m, 2H), 7.18-7.10 (m, 3H), 7.00-6.94 (m, 1H), 6.80-6.74 (m, 1H), 4.69(s, 2H), 3.27 (s, 3H).

$^1$H NMR (600 MHz, internal standard TMS, solvent DMSO) δ (ppm): 7.99 (s, 2H), 7.31-7.25(m, 2H), 7.24-7.16 (m, 4H), 7.07-7.01 (m, 1H), 6.94-6.88 (m, 1H), 4.88 (s, 2H), 3.18 (s, 3H).

LC-MS(m/z): 713.9 (m+H).

Example 9: Preparation of Compound 58.321

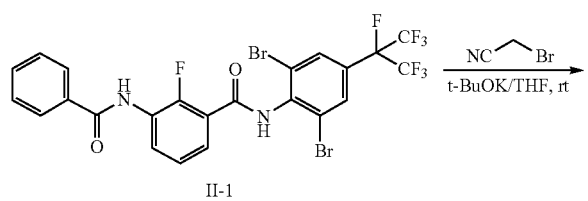

II-1

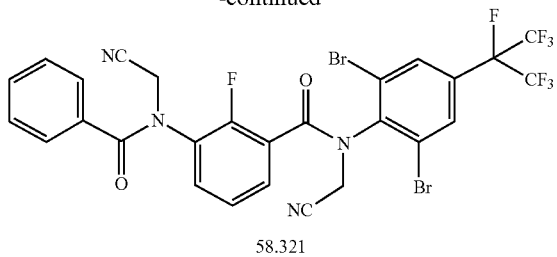

58.321

0.5 g (0.75 mmol) 3-benzamido-N-(2,6-dibromo-4-heptafluoroisopropylphenyl)-2-fluorobenzamide (intermediate II-1), 0.45 g (3.78 mmol) bromoacetonitrile and 0.42 g (3.75 mmol) potassium tert-butoxide were added to 20 ml tetrahydrofuran, and then stirred at room temperature for 5 h. By TLC monitoring, and at the end of the reaction, water and ethyl acetate were added for extraction; an obtained product was dried by anhydrous magnesium sulfate, filtered, and desolventized under reduced pressure; and residuals were purified by column chromatography (eluent was ethyl acetate and petroleum ether with the volume ratio of 1:6-1:2) to obtain 0.26 g white solid.

The nuclear magnetism and mass spectrometric data of the compound 58.321 were as follows: $^1$H NMR (600 MHz, internal standard TMS, solvent CDCl$_3$) δ (ppm): 7.77 (s, 2H), 7.33-7.28 (m, 3H), 7.18 (t, 2H), 7.16-7.12 (m, 1H), 7.09 (t, 1H), 6.82 (t, 1H), 5.05 (s, 1H), 4.69 (d, 2H), 4.20 (s, 1H). LC-MS(m/z): 760.9 (m+H).

Other compounds of Formula I of the present invention can be prepared by reference to the above Examples.

Determination of Biological Activity

Example 10: Determination of Insecticidal Activity

Experiments for the determination of the insecticidal activity of the compound against several kinds of pests were carried out. A determination method was as follows.

The compound to be tested was dissolved by a mixed solvent of acetone/methanol (1:1), and then diluted by water containing 0.1% (wt) Tween 80 to the required concentration.

An Airbrush spray method was adopted for the determination of the activity, with armyworm, Plutella xylostella and Chilo suppressalis as targets.

(1) Determination of insecticidal activity against armyworm

Determination method: maize blades were cut into 2 cm (length) segments; with the pressure of Airbrush spray being 10 psi (about 0.7 kg/cm$^2$), both sides of each blade segment were sprayed with the amount of 0.5 ml. After dried in the shade, each segment was inoculated with 10 3rd-instar larvas, 3 repeats for each segment. And then, the treated segments were put into an observation room (25° C., relative humidity: 60-70%) for cultivation; the number of the survivals was surveyed 1 d, 2 d and 3 d after administration, and then the death rate was calculated.

Partial test results with regard to armyworm were as follows:

the fatality rate of compounds 2.7, 2.17, 2.43, 2.321, 3.321, 6.321, 7.321, 8.321, 9.321, 16.321, 17.321, 20.321, 21.321, 30.321 and 58.321 against armyworm was 90% or more at a dose of 0.5 mg/L, 3 d after administration;

the fatality rate of compounds 2.7, 2.17, 2.43, 2.321, 3.321, 7.321, 8.321, 9.321, 16.321, 17.321, 21.321, 30.321 and 58.321 against armyworm was 90% ore more at a dose of 0.1 mg/L, 3 d after administration;

the fatality rate of compounds 2.7, 2.17, 2.43, 2.321, 9.321 and 30.321 against armyworm was 90% or more at a dose of 0.05 mg/L, 3 d after administration;

(2) Determination of insecticidal activity against Plutella xylostella

Determination method: cabbage blades were punched into 2 cm (diameter) leaf discs by a puncher; with the pressure of Airbrush spray being 10 psi (about 0.7 kg/cm$^2$), both sides of each leaf disc were sprayed with the amount of 0.5 ml. After dried in the shade, each leaf disc was inoculated with 10 3rd-instar larvaes, 3 repeats for each leaf disc. And then, the treated leaf discs were put into an observation room (25° C., relative humidity: 60-70%) for cultivation; the number of the survivals was surveyed 1 d, 2 d and 3 d after administration, and then the death rate was calculated.

Partial test results with regard to Plutella xylostella were as follows:

the fatality rate of compounds 2.7, 2.17, 2.43, 2.321, 3.321, 6.321, 7.321, 8.321, 9.321, 16.321, 17.321, 20.321, 21.321, and 58.321 against Plutella xylostella was 90% or more at a dose of 1 mg/L, 3 d after administration;

the fatality rate of compounds 2.7, 2.17, 2.43, 2.321, 9.321, 16.321, 30.321, and 58.321 against Plutella xylostella was 90% or more at a dose of 0.5 mg/L, 3 d after administration.

The fatality rate of compounds 9.321 and 30.321 against Plutella xylostella was 90% or more at a dose of 0.05 mg/L, 3 d after administration.

CK1, CK2, CK3 and CK4 were selected as control compounds, and compounds 2.7, 2.17, 2.43, 2.321, 3.321, 6.321, 7.321, 8.321, 9.321, 16.321, 17.321, 20.321, 21.321, 30.321 and 58.321 in the present invention were selected for a parallel comparison test for the insecticidal activity against Plutella xylostella (3 d after administration); the determination method was the same as described above; and the results were shown in table 71:

TABLE 71

Parallel comparison test for the insecticidal activity of partial compounds of the present invention and CK1-CK4 against plutella xylostella

| Compound No. | Fatality rate (%, 3 d after administration) 10 mg/L |
|---|---|
| 2.7 | 100 |
| 2.17 | 100 |
| 2.43 | 100 |
| 2.321 | 100 |
| 3.321 | 100 |
| 6.321 | 100 |
| 7.321 | 100 |
| 8.321 | 100 |
| 9.321 | 100 |
| 16.321 | 100 |
| 17.321 | 100 |
| 20.321 | 100 |
| 21.321 | 100 |
| 30.321 | 100 |
| 58.321 | 100 |
| CK1 | 0 |
| CK2 | 0 |
| CK3 | 0 |
| CK4 | 0 |

CK5, CK8 and CK12 were selected as control compounds, and compounds 6.321 and 20.321 in the present invention were selected for a parallel comparison test for the insecticidal activity against Plutella xylostella (3 d after administration); the determination method was the same as described above; and the results were shown in table 72:

TABLE 72

Parallel comparison test for the insecticidal activity of compounds 6.321 and 20.321 of the present invention and CK5, CK8, and CK12 against plutella xylostella

| Compound No. | Fatality rate (%, 3 d after administration) | |
|---|---|---|
| | 5 mg/L | 1 mg/L |
| 6.321 | 100 | 98.5 |
| 20.321 | 100 | 93.9 |
| CK5 | 63.5 | 0 |
| CK8 | 65.8 | 0 |
| CK12 | 60 | 0 |

CK6, CK9, CK10, CK13 and CK15 were selected as control compounds, and compounds 2.7, 2.17, 2.43, 2.321, 16.321, 30.321 and 58.321 in the present invention were selected for a parallel comparison test for the insecticidal activity against Plutella xylostella (3 d after administration); the determination method was the same as described above; and the results were shown in table 73:

TABLE 73

Parallel comparison test for the insecticidal activity of partial compounds of the present invention and CK6, CK9, CK10, CK13 and CK15 against plutella xylostella

| Compound No. | Fatality rate (%, 3 d after administration) | |
|---|---|---|
| | 1 mg/L | 0.5 mg/L |
| 2.7 | 100 | 100 |
| 2.17 | 100 | 100 |
| 2.43 | 100 | 100 |
| 2.321 | 100 | 100 |
| 16.321 | 100 | 100 |
| 30.321 | 100 | 100 |
| 58.321 | 100 | 98 |
| CK6 | 68 | 10 |
| CK9 | 55 | 0 |
| CK10 | 55 | 0 |
| CK13 | 75 | 0 |
| CK15 | 90 | 50 |

CK7, CK11, CK14 and CK16 were selected as control compounds, and compounds 9.321 and 30.321 in the present invention were selected for a parallel comparison test for the insecticidal activity against Plutella xylostella (3 d after administration); the determination method was the same as the above; and the results were shown in table 74:

TABLE 74

Parallel comparison test for the insecticidal activity of compounds 9.321 and 30.321 of the present invention and CK7, CK11 CK14, CK16 against plutella xylostella

| Compound No. | Fatality rate (%, 3 d after administration) | |
|---|---|---|
| | 0.5 mg/L | 0.05 mg/L |
| 9.321 | 100 | 100 |
| 30.321 | 100 | 100 |
| CK7 | 70 | 0 |
| CK11 | 75 | 0 |
| CK14 | 60 | 0 |
| CK16 | 100 | 80.8 |

CK15 was selected as a control compound, and compounds 2.321 and 30.321 in the present invention were selected for a parallel comparison test for the insecticidal activity against Plutella xylostella, so as to compare the fast-acting insecticidal efficacy; and the results were shown in table 75:

TABLE 75

Comparison test for the fast-acting insecticidal efficacy of compounds 2.321 and 30.321 of the present invention and CK15 against plutella xylostella

| Compound No. | Dose (mg/L) | Fatality rate (%) | | |
|---|---|---|---|---|
| | | 1 d after administration | 2 d after administration | 3 d after administration |
| 2.321 | 0.5 | 80 | 95 | 100 |
| 30.321 | 0.5 | 90 | 100 | 100 |
| CK15 | 0.5 | 0 | 30 | 50 |

It can be seen from table 75 that compared with the existing compound CK15, the compound of the present invention has more excellent fast-acting insecticidal efficacy and higher insecticidal activity at a lower dose.

CK16 was selected as a control compound, and compound 9.321 in the present invention was selected for a parallel comparison test for the insecticidal activity against Plutella xylostella, so as to compare the fast-acting insecticidal efficacy; and the results were shown in table 76:

TABLE 76

Comparison test for the fast-acting insecticidal efficacy of compound 9.321 of the present invention and CK16 against plutella xylostella

| Compound No. | Dose (mg/L) | Fatality rate (%) | | |
|---|---|---|---|---|
| | | 1 d after administration | 2 d after administration | 3 d after administration |
| 9.321 | 0.05 | 70 | 95 | 100 |
| CK16 | 0.05 | 0 | 52.5 | 80.8 |

It can be seen from table 76 that compared with the existing compound CK16, the compound of the present invention has more excellent fast-acting insecticidal efficacy and higher insecticidal activity at a lower dose.

(3) Determination of insecticidal activity against Chilo suppressalis

Determination method: 1) preparation of rice seedlings: rice was cultivated in small plastic cups (diameter: 4.5 cm and height: 4 cm) at a constant temperature room (temperature: 26-28° C., relative humidity: 60-80% around and illumination: 16 hL:8 hD), after the rice grew to a 4-5 leaf stage, vigorous and uniform-growth rice seedlings were selected and treated with an insecticide, 3 repeats for each treatment. 2) Preparation of pests for test: 3rd-instar larvaes of Chilo suppressalis fed continuously in the room. 3) Inoculation of pests on rice stems by spray. The whole plants of the rice seedlings were sprayed by a spray method uniformly, with the dose of 15 ml for each treatment. The blank control was treated first, and the above operation was repeated in an order of lower to higher test concentration. After sprayed, rice seedlings were placed in the shade to dry the insecticide liquor, and then stalks about 5 cm above the basal part of the stems were cut to be fed to the pests for test. Glass petri dishes (diameter: 9 mm) were prepared, cushioned by filter paper at the bottom thereof, and subjected to water addition for moisturizing; about 20 pieces of rice stems were put in each dish and inoculated with 10 larvaes; then the petri dishes were closed by non-woven fabrics and placed in a constant temperature room for culture. The number of survivals was surveyed 3 d after administration.

Partial test results with regard to Chilo suppressalis were as follows:

the fatality rate of compounds 2.7, 2.17, 2.43, 2.321, 3.321, 6.321, 7.321, 8.321, 9.321, 16.321, 17.321, 20.321, 21.321, 30.321 and 58.321 against Chilo suppressalis was 90% or more at a dose of 40 mg/L;

the fatality rate of compounds 2.7, 2.17, 2.43, 2.321, 3.321, 7.321, 8.321, 9.321, 16.321, 17.321, 21.321, 30.321 and 58.321 against Chilo suppressalis was 90% or more at a dose of 4 mg/L; the fatality rate of compounds 2.7, 2.17, 2.43, 2.321, 9.321 and 30.321 against Chilo suppressalis was 90% or more at a dose of 1 mg/L.

CK15 was selected as a control compound, and compounds 2.321 and 30.321 in the present invention were selected for a parallel comparison test for the insecticidal activity against Chilo suppressalis; the determination method was the same as described above; and the results were shown in table 77:

TABLE 77

Comparison of the insecticidal activity against chilo suppressalis between each of the compounds 2.321 and 30.321 in the present invention and CK15

| Compound No. | Fatality rate (%, 3 d after administration) | | |
|---|---|---|---|
| | 5 mg/L | 2.5 mg/L | 1.25 mg/L |
| 2.321 | 100 | 100 | 95.5 |
| 30.321 | 100 | 100 | 93.5 |
| CK15 | 50.3 | 22.2 | 8.6 |

It can be seen from table 77 that compared with the existing compound CK15, the compound of the present invention has the advantage of exerting better insecticidal efficacy at a lower dose. CK16 was selected as a control compound, and compound 9.321 in the present invention was selected for a parallel comparison test for the insecticidal activity against Chilo suppressalis; the determination method was the same as described above; and the results were shown in table 78:

TABLE 78

Comparison of the insecticidal activity against chilo suppressalis between compound 9.321 in the present invention and CK16

| Compound No. | Fatality rate (%, 3 d after administration) | | |
|---|---|---|---|
| | 2.5 mg/L | 1.25 mg/L | 0.625 mg/L |
| 9.321 | 100 | 100 | 98 |
| CK16 | 85.5 | 60.3 | 10 |

It can be seen from table 78 that compared with the existing compound CK16, the compound of the present invention has the advantage of exerting better insecticidal efficacy at a lower dose. The inventor of the present invention introduces a cyanomethyl ($CNCH_2$—) properly on the N atom of its amido bond on the basis of the molecular skeleton of the existing compound, thus obtaining the compound of Formula I of the present invention. It can be seen from data of the comparison tests of tables 71-78 that the introduction of a new proper segment (an efficacy group) increases the opportunity of a molecule to interact and bond with a receptor; therefore, the compound of the present invention has unexpected effect relative to the existing compounds. That is, the compound of the present invention has higher insecticidal activity and more excellent fast-acting insecticidal efficacy (the compound of the present invention takes effect rapidly, and can achieve higher insecticidal activity 1 d after application, and extremely high insecticidal activity within 3 d).

In organic molecules, due to the difference of substituents in electronegativity, volume or steric configuration, there is a marked variation in conductivity or receptor binding capacity of the whole molecule in biological bodies, such as insects and plants, and accordingly, the molecule shows obvious difference in biological activity. Moreover, the conductivity or receptor binding appropriateness of the molecule cannot be expected, and can be obtained in need of a large amount of creative efforts. Therefore, the present invention possesses substantive features and significant progress.

The invention claimed is:

1. A benzamide compound, as shown in Formula I:

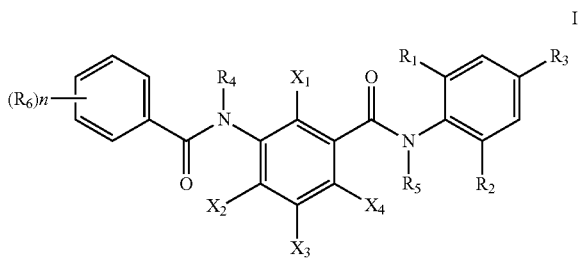

in the formula:
$R_1$ and $R_2$ are each independently selected from H, halogen, $C_1$-$C_6$ alkyl, $C_1$-$C_6$ haloalkyl, $C_1$-$C_6$ alkoxy or $C_1$-$C_6$ haloalkoxy;
$R_3$ is selected from heptafluoroisopropyl or nonafluoro-2-butyl;
$R_4$ and $R_5$ are each independently selected from H, $C_1$-$C_6$ alkyl, $C_1$-$C_6$ haloalkyl or cyanomethyl;
moreover, at least one of $R_4$ and $R_5$ is selected from cyanomethyl;
$R_6$ is selected from H, halogen, cyano, nitryl, $C_1$-$C_6$ alkyl, $C_1$-$C_6$ haloalkyl, $C_1$-$C_6$ alkoxy or $C_1$-$C_6$ haloalkoxy; $C_1$-$C_6$ alkylthio or $C_1$-$C_6$ haloalkylthio; n=1, 2, 3, 4 or 5;
$X_1$, $X_2$, $X_3$, and $X_4$ are each independently selected from H, halogen, cyano or $C_1$-$C_6$ alkoxy; and,
$X_1$, $X_2$, $X_3$, and $X_4$ are not simultaneously H.

2. The compound according to claim 1, wherein, in the Formula I,
$R_1$ and $R_2$ are each independently selected from H, halogen, $C_1$-$C_4$ alkyl, $C_1$-$C_4$ haloalkyl, $C_1$-$C_4$ alkoxy or $C_1$-$C_4$ haloalkoxy;
$R_3$ is selected from heptafluoroisopropyl or nonafluoro-2-butyl;
$R_4$ and $R_5$ are each independently selected from H, methyl, ethyl or cyanomethyl; moreover, at least one of $R_4$ and $R_5$ is selected from cyanomethyl;
$R_6$ is selected from H, halogen, cyano, nitryl, $C_1$-$C_4$ alkyl, $C_1$-$C_4$ haloalkyl, $C_1$-$C_4$ alkoxy or $C_1$-$C_4$ haloalkoxy; $C_1$-$C_4$ alkylthio or $C_1$-$C_4$ haloalkylthio; n=1, 2, 3, or 4;
$X_1$ is selected from F;
$X_2$, $X_3$, and $X_4$ are each independently selected from H, F or cyano.

3. The compound according to claim 2, wherein, in the Formula I,
$R_1$ and $R_2$ are each independently selected from H, halogen, methyl, ethyl, trifluoromethyl or difluoromethoxy;
$R_3$ is selected from heptafluoroisopropyl or nonafluoro-2-butyl;
$R_4$ and $R_5$ are each independently selected from H, methyl, ethyl or cyanomethyl; moreover, at least one of $R_4$ and $R_5$ is selected from cyanomethyl;
$R_6$ is selected from H, F, Cl, Br, cyano, nitryl, methyl, ethyl, propyl, tertiary butyl, trifluoromethyl, heptafluoroisopropyl, methoxy or trifluoromethoxy; n=1, 2 or 3;
$X_1$ is selected from F;
$X_2$, $X_3$, and $X_4$ are each independently selected from H, or F.

4. The compound according to claim 1, wherein, in the Formula I,
$R_1$ and $R_2$ are each independently selected from H, halogen, methyl, ethyl, trifluoromethyl or difluoromethoxy;
$R_3$ is selected from heptafluoroisopropyl or nonafluoro-2-butyl;
$R_4$ is selected from cyanomethyl;
$R_5$ is selected from H, methyl, ethyl or cyanomethyl;
$R_6$ is selected from H, F, Cl, Br, cyano, nitryl, methyl, ethyl, propyl, tertiary butyl, trifluoromethyl, heptafluoroisopropyl, methoxy or trifluoromethoxy; n=1, 2 or 3;
$X_1$ is selected from F;
$X_2$, $X_3$, and $X_4$ are each independently selected from H, or F.

5. The compound according to claim 1, wherein, in the Formula I,
$R_1$ and $R_2$ are each independently selected from H, halogen, methyl, ethyl, trifluoromethyl or difluoromethoxy;
$R_3$ is selected from heptafluoroisopropyl or nonafluoro-2-butyl;
$R_4$ is selected from H, methyl, or ethyl;
$R_5$ is selected from cyanomethyl;
$R_6$ is selected from H, F, Cl, Br, cyano, nitryl, methyl, ethyl, propyl, tertiary butyl, trifluoromethyl, heptafluoroisopropyl, methoxy or trifluoromethoxy; n=1, 2 or 3;
$X_1$ is selected from F;
$X_2$, $X_3$, and $X_4$ are each independently selected from H, or F.

6. An insecticidal composition, wherein the composition comprises the compound of Formula I according to claim 1 as an active component; the percentage by weight of the active component in the composition is within 0.1-99%.

7. A method of controlling pests in agriculture and forestry, wherein an effective amount of the composition according to claim 6 is applied to a pest to be controlled or onto a growth medium thereof.

* * * * *